(12) United States Patent
Yokozeki et al.

(10) Patent No.: US 7,749,742 B2
(45) Date of Patent: Jul. 6, 2010

(54) METHOD FOR PRODUCING TRIPEPTIDES AND/OR PEPTIDES LONGER THAN TRIPEPTIDES

(75) Inventors: Kenzo Yokozeki, Kanagawa (JP); Sonoko Suzuki, Kanagawa (JP); Seiichi Hara, Kanagawa (JP); Isao Abe, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 193 days.

(21) Appl. No.: 11/940,555

(22) Filed: Nov. 15, 2007

(65) Prior Publication Data

US 2008/0171357 A1 Jul. 17, 2008

Related U.S. Application Data

(60) Division of application No. 10/849,814, filed on May 21, 2004, now Pat. No. 7,338,780, which is a continuation of application No. PCT/JP03/09466, filed on Jul. 25, 2003.

(30) Foreign Application Priority Data

Jul. 26, 2002 (JP) .............................. 2002-218958

(51) Int. Cl.
C12N 9/10 (2006.01)
C12N 1/20 (2006.01)
C12N 15/00 (2006.01)
C12P 21/06 (2006.01)
C12P 13/04 (2006.01)
A61K 38/00 (2006.01)
C07H 21/04 (2006.01)

(52) U.S. Cl. .................... 435/193; 435/69.1; 435/320.1; 435/252.3; 435/68.1; 435/106; 435/15; 530/300; 530/331; 530/333; 536/23.2

(58) Field of Classification Search ........................ None
See application file for complete search history.

(56) References Cited

U.S. PATENT DOCUMENTS 5,968,767 A 10/1999 Sheikh et al.
6,143,517 A 11/2000 Young

FOREIGN PATENT DOCUMENTS

| EP | 0 209 430 | 1/1987 |
|---|---|---|
| EP | 0 278 787 | 8/1988 |
| EP | 0 302 442 | 2/1989 |
| EP | 0 359 399 | 3/1990 |
| JP | 49-69888 | 7/1974 |
| JP | 53-92729 | 8/1978 |
| JP | 62-48697 | 3/1987 |
| JP | 1-96194 | 4/1989 |
| JP | 1-104192 | 4/1989 |
| JP | 1-502158 | 8/1989 |
| JP | 02-104281 A | 4/1990 |
| JP | 4-501056 | 2/1992 |
| JP | 6-234715 | 8/1994 |
| JP | 6-237784 | 8/1994 |
| JP | 2000-078971 A | 3/2000 |
| JP | 4273967 B2 | 3/2009 |
| WO | 90/01555 | 2/1990 |
| WO | WO 03/010189 A1 | 2/2003 |

OTHER PUBLICATIONS

Linne et al., Control of directionality in Nonribosomal peptide synthesis: Role of the condensation domain in preventing misinitiation and timing of epimerization. Biochemistry, 2000, vol. 39: 10439-10447.*

J. J. Polderman-Tijames, et al., "Cloning, Sequence Analysis, and Expression in *Escherichia coli* of the Gene Encoding and Alpha-Amino Acid Ester Hydrolase From *Acetobacter turbidans*," Applied and Environmental Microbilogy, vol. 68, No. 1, Jan. 2002, pp. 211-218.

A. J. Simpson, et al., "The Genome Sequence of the Plant Pathogen Xylella Fastidiosa," Nature, vol. 406, No. 6792, Jul. 13, 2000, pp. 151-157, entry H82731.

S. Akabori, et al., "Protection of Amide-Nitrogen for Peptide Synthesis. A Novel Synthesis of Peptides Containing C-Terminal Glutamine," Bull. Chem. Soc. Jpn., 34, May 1961, p. 739.

Y. Shimonishi, et al., "Studies on the Synthesis of Peptides Containing Glutamine as the C-Terminal. I. Protection of Amide-Nitrogen With Xanthyl Group During Peptide Synthesis," Bull. Chem. Soc. Jpn., vol. 35, No. 12, Dec. 1962, pp. 1966-1970.

Y. Shimonishi, "Studies of the Synthesis of Peptides Containing C-Terminal Glutamine. II. The Synthesis and Use of α-p-Nitrobenzyl, γ-Methyl L-Glutamate", Bull. Chem. Soc. Jpn. vol. 37, No. 2, Feb. 1964, pp. 200-203.

K. Morihara, et al., "Alpha-Chymotrypsin as the Catalyst for Peptide Synthesis", Biochem. J., (1977), 163, pp. 531-542.

K. Yokozeki, et al., "A Novel and Efficient Enzymatic Method for the Production of Peptides From Unprotected Starting Materials," Journal of Biotechnology, vol. 115, No. 2, Jan. 26, 2005, pp. 211-220, XP-002348456.

* cited by examiner

*Primary Examiner*—Ganapathirama Raghu
(74) *Attorney, Agent, or Firm*—Oblon, Spivak, McClelland, Maier & Neustadt, L.L.P.

(57) ABSTRACT

A method is disclosed that allows the production of peptides having three or more amino acid residues easily, inexpensively and at high yield without going through a complex synthesis method. A novel enzyme that efficiently produces a peptide from bacteria belonging to the genus *Empedobacter* or the genus *Sphingobacterium* is provided. The enzyme acts on a carboxy component and an amine component to form peptides having three or more amino acid residues by acting on a carboxy component and an amine component.

11 Claims, 4 Drawing Sheets

METHOD FOR PRODUCING TRIPEPTIDES AND/OR PEPTIDES LONGER THAN TRIPEPTIDES

CROSS-REFERENCE TO RELATED APPLICATIONS

The present application is a divisional of U.S. application Ser. No. 10/849,814 (now U.S. Pat. No. 7.338.780), filed on May 21, 2004, which is a continuation of PCT/JP03/09466, filed on Jul. 25, 2003, and claims priority to JP 2002-218958, filed on Jul. 26, 2002.

TECHNICAL FIELD

The present invention relates to a method for producing peptides that can produce peptides easily, inexpensively and at high yield without going through a complex synthetic method. More particularly, the present invention relates to a method for producing peptides that are equal to or longer than tripeptides by using an enzyme that catalyzes a peptide-forming reaction from a carboxy component and an amine component.

BACKGROUND ART

Peptides are used in the fields of pharmaceuticals, foods and various other fields. For example, since L-alanyl-L-glutamine has higher stability and water-solubility than L-glutamine, it is widely used as a component of fluid infusion and serum-free media.

Chemical synthesis methods, which have been known as methods for producing peptides, are not always easy. Known examples of such methods include a method that uses N-benzyloxycarbonylalanine (hereinafter, "Z-alanine") and protected L-glutamine (see Bull. Chem. Soc. Jpn., 34, 739 (1961), Bull. Chem. Soc. Jpn., 35, 1966 (1962)), a method that uses Z-alanine and protected L-glutamic acid-γ-methyl ester (see Bull. Chem. Soc. Jpn., 37, 200 (1964)), a method that uses Z-alanine ester and unprotected glutamic acid (see Japanese Patent Application Laid-open Publication No. H1-96194), a method that involves synthesis of an N-(2-substituted)-propionyl glutamine derivative as an intermediate from a 2-substituted-propionyl halide as a raw material (see Patent Application Laid-open Publication No. H6-234715).

However, since all of these methods require the introduction and elimination of protecting groups or the use of an optically active intermediate, they are not considered to be adequately satisfactory in terms of their industrial advantages.

On the other hand, widely known examples of typical peptide production methods using enzymes consist of a condensation reaction that uses an N-protected, C-unprotected carboxy component and an N-unprotected, C-protected amine component (hereinafter, "Reaction 1"), and a substitution reaction that uses an N-protected, C-protected carboxy component and an N-unprotected, C-protected amine component (hereinafter, "Reaction 2"). An example of Reaction 1 is a method for producing Z-aspartylphenylalanine methyl ester from Z-aspartic acid and phenylalanine methyl ester (see Japanese Patent Application Laid-open Publication No. S53-92729), while an example of Reaction 2 is a method for producing acetylphenylalanylleucine amide from acetylphenylalanine ethyl ester and leucine amide (see Biochemical J., 163, 531 (1977)). There have been reported very few research examples of methods that use an N-unprotected, C-protected carboxy component. An example of a substitution reaction that uses an N-unprotected, C-protected carboxy component and an N-unprotected, C-protected amine component (hereinafter, "Reaction 3") is described in International Patent Publication WO 90/01555. For example, a method for producing arginylleucine amide from arginine ethyl ester and leucine amide may be mentioned of. Examples of substitution reactions that use an N-unprotected, C-protected carboxy component and an N-unprotected, C-unprotected amine component (hereinafter, "Reaction 4") are described in European Patent Publications EP 278787A1 and EP 359399B1. For example, a method for producing tyrosylalanine from tyrosine ethyl ester and alanine may be mentioned of.

DISCLOSURE OF THE INVENTION

The most inexpensive production method among the aforementioned methods of Reactions 1 to 4 naturally falls within the class of Reaction 4, which involves the fewest protecting groups.

However, the example of Reaction 4 of the prior art (European Patent Publication EP 278787A1) had the following major problems: (1) extremely slow rate of peptide production, (2) low peptide production yield, (3) the peptides that can be produced are limited to those that contain amino acids with comparatively high hydrophobicity, (4) the amount of enzyme added is extremely large, and (5) comparatively expensive carboxypeptidase preparations derived from molds, yeasts or plants are required. In the Reaction 4, there is no method known whatsoever that uses an enzyme derived from bacteria or yeasts other than the genus *Saccharomyces*, and there is no known method for producing alanylglutamine and other peptides that are highly hydrophilic. In consideration of this background, there is a need to develop an industrially inexpensive method for producing these peptides.

In addition, the method for producing peptides of the Reaction 4 that uses an enzyme is limited to the formation of dipeptides, and there has been a need to develop a method for simply and easily producing peptides that are equal to or longer than tripeptides so that they can be adequately used industrially.

Under the circumstances, it is an object of the present invention to provide a method that can produce peptides that are equal to or longer than tripeptides to easily, inexpensively and at high yield without going through a complex synthesis method.

As a result of conducting extensive research in consideration of the aforementioned object, the inventors of the present invention have discovered an enzyme that efficiently forms peptides that are equal to or longer than tripeptides from newly discovered bacteria belonging to the genus *Empedobacter* and bacteria belonging to the genus *Sphingobacterium*, and have completed the present invention.

Namely, the present invention is as described below.

[1] A method for producing a peptide having three or more amino acid residues including the step of forming the peptide having three or more amino acid residues with an enzyme or enzyme-containing substance, wherein the enzyme or enzyme-containing substrate has an ability to use as substrates an amine component having two or more amino acid residues and a carboxy component, to form a peptide having one more peptide bond than the amine component.

[2] The method for producing a peptide according to [1], wherein the enzyme or enzyme-containing substance includes one type or two or more types selected from the group consisting of a culture of a microbe, microbial cells separated from the culture, and a treated microbial cell product of the microbe which have the ability to use as substrates an amine component having two or more amino acid residues and a carboxy component, to form a peptide having one more peptide bond than the amine component.

[3] The method for producing a peptide according to [1] or [2], wherein the enzyme or enzyme-containing substance is able to use as the carboxy component both an amino acid ester and an amino acid amide.

[4] The method for producing a peptide according to any one of [1] to [3], wherein the enzyme or enzyme-containing substance is able to use as the amine component any of (i) an unprotected peptide having two or more amino acid residues, (ii) a C-protected peptide having two or more amino acid residues, and (iii) a peptide having two or more amino acid residues whose C-terminal molecule is an amine instead of an amino acid.

[5] The method for producing a peptide according to [1], wherein the enzyme is a protein (A) or (B):
 (A) a protein having an amino acid sequence consisting of amino acid residues numbers 23-616 of an amino acid sequence described in SEQ ID NO: 6 of the Sequence Listing,
 (B) a protein having an amino acid sequence including substitution, deletion, insertion, addition, and/or inversion of one or a plurality of amino acids in the amino acid sequence consisting of amino acid residues 23 to 616 of the amino acid sequence described in SEQ ID NO: 6 of the Sequence Listing, and having activity to use as substrates an amine component having two or more amino acid residues and a carboxy component, to form a peptide having one more peptide bond than the amine component.

[6] The method for producing a peptide according to [1], wherein the enzyme is a protein (C) or (D):
 (C) a protein having an amino acid sequence consisting of amino acid residues numbers 21 to 619 of an amino acid sequence described in SEQ ID NO: 12 of the Sequence Listing,
 (D) a protein having an amino acid sequence including substitution, deletion, insertion, addition, and/or inversion of one or a plurality of amino acids in the amino acid sequence consisting of amino acid residues 21 to 619 of the amino acid sequence described in SEQ ID NO: 12 of the Sequence Listing, and having activity to use as substrates an amine component having two or more amino acid residues and a carboxy component, to form a peptide having one more peptide bond than the amine component.

[7] The method for producing a peptide according to [1], wherein the enzyme is a protein (E) or (F):
 (E) a protein having an amino acid sequence described in SEQ ID NO: 6 of the Sequence Listing,
 (F) a protein containing a mature protein region, the protein having an amino acid sequence including substitution, deletion, insertion, addition, and/or inversion of one or a plurality of amino acids in the amino acid sequence described in SEQ ID NO: 6 of the Sequence Listing, and having activity to use as substrates an amine component having two or more amino acid residues and a carboxy component, to form a peptide having one more peptide bond than the amine component.

[8] The method for producing a peptide according to [1], wherein the enzyme is a protein (G) or (H):
 (G) a protein having an amino acid sequence described in SEQ ID NO: 12 of the Sequence Listing,
 (H) a protein containing a mature protein region, the protein having an amino acid sequence including substitution, deletion, insertion, addition, and/or inversion of one or a plurality of amino acids in the amino acid sequence described in SEQ ID NO: 12 of the Sequence Listing but contains therein substitution, deletion, insertion, addition and/or inversion of one or a plurality of amino acids and having activity to use as substrates an amine component having two or more amino acid residues and a carboxy component, to form a peptide having one more peptide bond than the amine component.

[9] The method for producing a peptide according to [2], wherein the microbe is a microbe belonging to the genus *Empedobacteror* belonging to the genus *Sphingobacterium*.

[10] The method for producing a peptide according to [2], wherein the microbe is a microbe that has been transformed so as to be able to express a protein encoded by a DNA (a) or (b):
 (a) a DNA that having a base sequence consisting of bases numbers 127 to 1908 of a base sequence described in SEQ ID NO: 5 of the Sequence Listing,
 (b) a DNA that hybridizes with a DNA having a base sequence complementary to the base sequence consisting of bases numbers 127 to 1908 of the base sequence described in SEQ ID NO: 5 of the Sequence Listing under stringent conditions, and encodes a protein that has peptide-forming activity.

[11] The method for producing a peptide according to [2], wherein the microbe is a microbe that has been transformed so as to be able to express a protein encoded by a DNA (c) or (d):
 (c) a DNA that consists of bases numbers 121 to 1917 of a base sequence described in SEQ ID NO: 11 of the Sequence Listing,
 (d) a DNA that hybridizes with a DNA having a base sequence complementary to the base sequence consisting of bases numbers 121 to 1917 of the base sequence described in SEQ ID NO: 11 of the Sequence Listing under stringent conditions, and encodes a protein that has peptide-forming activity.

[12] The method for producing a peptide according to [2], wherein the microbe is a microbe that has been transformed so as to be able to express protein encoded by a DNA (e) or (f):
 (e) a DNA that consists of bases numbers 61 to 1908 of a base sequence described in SEQ ID NO: 5 of the Sequence Listing,
 (f) a DNA that hybridizes with a DNA having a base sequence complementary to the base sequence consisting of bases numbers 61 to 1908 of the base sequence described in SEQ ID NO: 5 of the Sequence Listing under stringent conditions, and encodes a protein that has peptide-forming activity.

[13] The method for producing a peptide according to [2], wherein the microbe is a microbe that has been transformed so as to be able to express a protein encoded by a DNA (g) or (h):
 (g) a DNA that consists of bases numbers 61 to 1917 of a base sequence described in SEQ ID NO: 11 of the Sequence Listing,
 (h) a DNA that hybridizes with a DNA that consisting of a base sequence complementary to the base sequence consisting of bases numbers 61 to 1917 of the base sequence described in SEQ ID NO: 11 of the Sequence Listing under stringent conditions, and encodes a protein that contains a mature protein region that has peptide-forming activity.

[14] The method for producing a peptide according to any one of [1] to [13], wherein the carboxy component comprises one type or two or more types selected from the group consisting of an L-alanine ester, a glycine ester, an L-threonine ester, an L-tyrosine ester and a D-alanine ester.

BEST MODE FOR CARRYING OUT THE INVENTION

Figure 1:
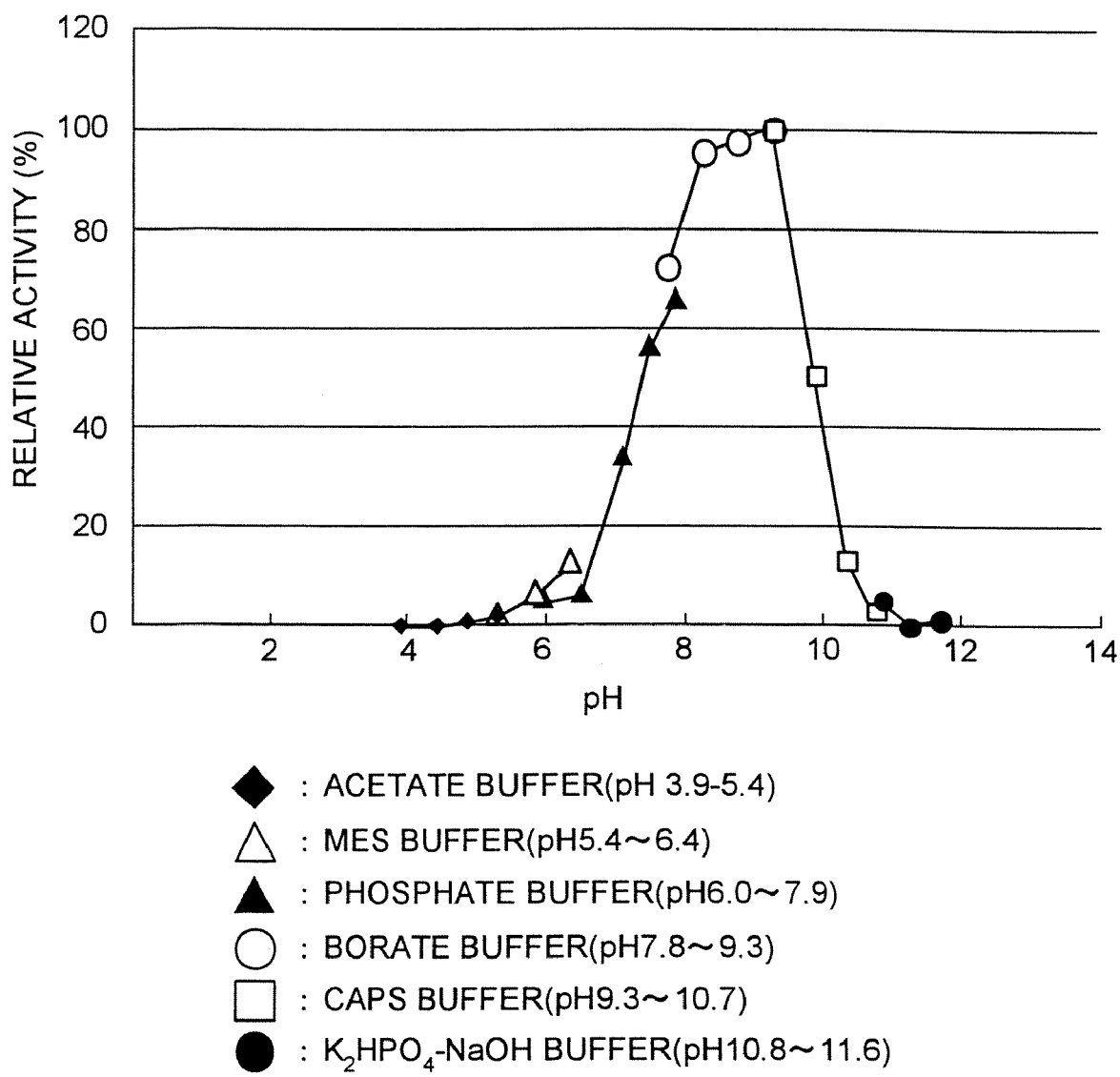
FIG. 1 shows the optimum pH of an enzyme of *Empedobacter*.

The method for producing a peptide that is equal to or longer than a tripeptide according to the present invention is explained in detail in the order of:
1. Method for Producing Peptides that are Equal to or Longer than Tripeptides, and
2. Enzyme Used in the Present Invention.

In the present specification, the carboxy component refers to the component that provides a carbonyl site (CO) in the peptide bond (—CONH—), while the amine component refers to the component that provides the amino site (NH) in the peptide bond. In addition, in the present specification, the term "peptide" when used alone refers to a polymer having at least one peptide bond unless otherwise indicated specifically. Further, the term "dipeptide" herein refers to a peptide having one peptide bond. Moreover, the term "a peptide that is equal to or longer than a tripeptide" herein refers to a peptide having two or more peptide bonds.

1. Method for Producing Peptides that are Equal to or Longer than Tripeptides

In the method for producing peptides that are equal to or longer than tripeptides according to the present invention (hereinafter also referred to "peptide production method of the present invention"), a carboxy component and an amine component are allowed to react in the presence of a predetermined enzyme. That is to say, the method for producing peptides according to the present invention employs an enzyme or an enzyme-containing substance that has the ability to form a peptide having one more peptide bond than the amine component, from the amine component equal to or longer than a dipeptide and the carboxy component. That enzyme or enzyme-containing substance acts on the carboxy component and the amine component, to produce the peptide that is equal to or longer than a tripeptide.

The action of the enzyme or enzyme-containing substance on the carboxy component and on the amine component may be accomplished merely by mixing the enzyme or enzyme-containing substance, the carboxy component and the amine component. More specifically, a method by adding an enzyme or enzyme-containing substance to a solution containing the carboxy component and the amine component and allowing the resultant to react can be used. Alternatively, in the case of using a microbe that produces the enzyme, a method by adding the carboxy component and amine component to a microbial culture broth after the enzyme was produced and accumulated in the microbial cells or in the culture broth can be used. If necessary, the produced peptide that is equal to or longer than a tripeptide can then be recovered and purified by conventional methods.

The term "enzyme-containing substance" means any substance so far as it contains the enzyme, and examples of specific forms thereof include a microbial culture broth containing the enzyme, microbial cells isolated from the culture, and a product obtained by treating microbial cells (hereinafter, "treated microbial cell product"). A microbial culture broth refers to what is obtained by culturing a microbe, and more specifically, to a mixture of microbial cells, medium used for culturing the microbe and substances produced by the cultured microbe, and so forth. In addition, the microbial cells can be used in the form of washed microbial cells. In addition, the treated microbial cell product includes disrupted, lysed or freeze-dried microbial cells, and the like, and also includes a crude enzyme recovered from treated microbial cells, and a purified enzyme obtained by purification of the crude enzyme, and so forth. A partially purified enzyme obtained by various purification methods may be used as the purified enzyme, or immobilized enzymes may be used that have been immobilized by a covalent bonding method, an adsorption method or an entrapment method. In addition, since some microbes are partially lysed during culturing depending on the microbes used, in such cases, the culture supernatant may also be used as the enzyme-containing substance.

In addition, wild strains may be used for the microbes that contain the enzyme, or recombinant strains that express the enzyme obtained by genetic engineering may also be used. The microbes are not limited to intact microbial cells, but rather acetone-treated microbial cells, freeze-dried microbial cells or other treated microbial cells may also be used. Immobilized microbial cells and an immobilized treated microbial cell product obtained by immobilization by covalent bonding, adsorption, entrapment or other methods, may also be used.

Use of a wild strain producing a peptide-forming enzyme having activity to form a peptide, that is equal to or longer than a tripeptide, is rather preferable since the trouble of construction of a recombinant strain by genetic engineering and so forth is eliminated and a peptide is produced more easily. On the other hand, a recombinant strain obtained by genetic engineering that has been transformed to express a peptide-forming enzyme having activity to form a peptide that is equal to or longer than a tripeptide can produce a larger amount of a peptide. So, synthesis of peptides that are equal to or longer than tripeptides can be carried out more rapidly in large amounts. Peptides that are equal to or longer than tripeptides can be produced by mixing amino acid esters and amine component with wild or recombinant microbial culture broth and/or wild or recombinant microbial cells which is cultured in the medium.

In addition, in the case of microbial culture broth, cultured microbial cells, washed microbial cells or a treated microbial cell product that has been obtained by disrupting or lysing microbial cells, there are many cases in which an existing enzyme does not participate in peptide formation but decomposes the formed peptides. In this situation, it may be rather preferable in some cases to add a metal protease inhibitor such as ethylenediaminetetraacetic acid (EDTA). The addition amount is within the range of 0.1 millimolar (mM) to 300 mM, and preferably 1 mM to 100 mM.

The amount of enzyme or enzyme-containing substance used may be enough if its amount is effective for peptide production (effective amount). This effective amount can be easily determined through simple and preliminary experimentation by a person with ordinary skill in the art. In the case of using the enzyme, for example, the effective amount is about 0.01 to about 100 units (U), while in the case of using washed microbial cells, the effective amount is about 1 to about 500 grams per liter (g/L).

Any carboxy component may be used so far as it can form a peptide by condensation with the amine component that is the other substrate. Examples of the carboxy component include L-amino acid esters, D-amino acid esters, L-amino acid amides and D-amino acid amides. In addition, examples of the amino acid esters or amino acid amides include amino acid esters or amino acid amides corresponding to not only naturally-occurring amino acids, but also corresponding to non-naturally-occurring amino acids or their derivatives. In addition, examples of the amino acid esters or amino acid amides include not only α-amino acid esters or α-amino acid amides but also β-, γ- and ω- etc. amino acid esters or β-, γ- and ω- etc. amino acid amides, which have different binding sites of amino groups. Typical examples of the amino acid ester include methyl esters, ethyl esters, n-propyl esters, iso-propyl esters, n-butyl esters, iso-butyl esters, and tert-butyl esters, etc. of amino acids.

Any peptide may be used for the amine component so far as it can form a peptide by condensation with the carboxy component that is the other substrate. The minimum unit of the amine component is a dipeptide, while there is no particular upper limit therefor. In addition, there is also no particular restriction on the amino acid sequence of the peptide serving as the amine component. In addition, the peptide used as the amine component may include the one whose side chain was modified, or one that contains amines instead of the amino acids. More specifically, examples of the amine component include C-unprotected peptides being equal to or longer than dipeptides, C-protected peptides being equal to or longer than dipeptides, and peptides being equal to or longer than dipeptides, in which the C-terminal molecule is an amine instead of the amino acid. For example, structure of a tripeptide that is equal to or longer than a dipeptide in which the C-terminal molecule is an amine instead of an amino acid is described as N-terminal amino acid—amino acid—amine.

Although the concentrations of the carboxy component and amine component serving as starting materials are 1 mM to 10 molars (M), and preferably 0.05 M to 2 M, respectively, there are cases in which it is preferable to add the amine component in an amount equimolar or excess molar with respect to the carboxy component. In addition, when high concentrations of substrates inhibit the reaction, step-wise addition without inhibition can be used during the reaction.

The reaction temperature that allows formation of a peptide is 0 to 60° C., and preferably 5 to 40° C. The reaction pH that allows formation of a peptide is 6.5 to 10.5, and preferably 7.0 to 10.0.

To produce a peptide being equal to or longer than a tripeptide having a desired amino acid sequence, it is sufficient that amino acid esters serving as the carboxy components be selected step-wisely to make the desired amino acid sequence, with which the amino acid sequence may be successively extended. For example, to produce a tripeptide, L-Ala-L-His-L-Ala, the tripeptide may be synthesized by using alanine methyl ester as the carboxy component and by using a dipeptide, L-His-L-Ala, as the amine component. After formation of the tripeptide, a peptide, Gly-L-Ala-L-His-L-Ala, can be obtained by adding glycine methyl ester as the carboxy component with the above tripeptide as the amine component.

2. Enzyme Used in the Present Invention

The aforementioned peptide production method of the present invention employs an enzyme having the ability to form a peptide having one more peptide bond than the amine component from the carboxy component and the peptide being equal to or longer than a dipeptide as the amine component. In the peptide production method of the present invention, there is no particular restriction on the origin or the obtaining method and so forth of the enzyme so far as the enzyme has this activity. Hereinafter, microbes having the enzymes that can be used in the present invention, cultivation of the microbes, purification of the enzymes, and application of genetic engineering techniques will be explained.

(2-1) Microbes having Enzyme that can be Used in the Production Method of the Present Invention Examples of microbes that form the enzyme of the present invention include bacteria belonging to the genus *Empedobacter* and bacteria belonging to the genus *Sphingobacterium*, and more specifically include *Empedobacter brevis* ATCC 14234 strain (FERM P-18545 strain, FERM BP-8113 strain) and *Sphingobacterium* sp. strain FERM BP-8124. *Empedobacter* brevisATCC 14234 strain (FERM P-18545 strain, FERM BP-8113 strain) and *Sphingobacterium* sp. FERM BP-8124 strain are microbes that the inventors of the present invention isolated through the screening of microbes that produce a peptide from a carboxy component and an amine component in high yield.

*Empedobacter brevis* ATCC 14234 strain (FERM P-18545 strain, FERM BP-8113 strain) was deposited at the International Patent Organism Depositary of the independent administrative corporation, National Institute of Advanced Industrial Science and Technology (Chuo Dai-6, 1-1 Higashi 1-Chome, Tsukuba-shi, Ibaraki-ken, Japan) on Oct. 1, 2001 and assigned the deposit number of FERM P-18545. Control of this organism was subsequently transferred to deposition under the provisions of the Budapest Treaty at the International Patent Organism Depositary of the independent administrative corporation, National Institute of Advanced Industrial Science and Technology on Jul. 8, 2002 and was assigned the deposit number of FERM BP-8113 (indication of microbe: *Empedobacter brevis* AJ 13933 strain).

*Sphingobacterium* sp. AJ 110003 strain was deposited at the International Patent Organism Depositary of the independent administrative corporation, National Institute of Advanced Industrial Science and Technology (Chuo Dai-6, 1-1 Higashi 1-Chome, Tsukuba-shi, Ibaraki-ken, Japan) on Jul. 22, 2002, and was assigned the deposit number of FERM BP-8124. In addition, the strain AJ 110003 (FERM BP-8124) was identified to be the aforementioned *Sphingomonas* sp. by the identification experiment described hereinbelow. The strain FERM BP-8124 is a Gram-negative rod (0.7 to 0.8×1.5 to 2.0 μm) that forms no spore and is not motile. Its colonies are, round with a completely smooth border, contain low protrusions, have a glossy and light yellow color. The strain FERM BP-8124 grows at 30° C. and is catalase positive, oxidase positive and the OF test (glucose) negative. Judging from these results, this strain was identified as a bacterium belonging to the genus *Sphingobacterium*. Moreover, from the properties that nitrate reduction is negative, indole production is negative, acid production from glucose is negative, arginine dihydrolase is negative, urease is positive, esculin hydrolysis is positive, gelatin hydrolysis is negative, β-galactosidase is positive, glucose assimilation is positive, L-arabinose assimilation is negative, D-mannose assimilation is positive, D-mannitol assimilation is negative, N-acetyl-D-glucosamine assimilation is positive, maltose assimilation is positive, potassium gluconate assimilation is negative, n-capric acid assimilation is negative, adipic acid assimilation is negative, dl-malic acid assimilation is negative, sodium citrate assimilation is negative, phenyl acetate assimilation is negative and cytochrome oxidase is positive, it was determined to have properties that are similar to those of *Sphingobacterium multivorum* or *Sphingobacterium spiritivorum*. Moreover, although results of analyses on the homology of the base sequence of the 16S rRNA gene indicate the highest degree of homology with *Sphingobacterium multivorum* (98.8%), there was no strain with which the bacterial strain matched completely. Accordingly, this bacterial strain was identified as *Sphingobacterium* sp.

(2-2) Cultivation of Microbe

To obtain cultured cells of microbes having the enzyme used in the present invention, it suffices that the microbes is cultured and grown in a suitable medium. There is no particular restriction on the medium used for this purpose so far as it is allows the microbes to grow. This medium may be an ordinary medium containing ordinary carbon sources, nitrogen sources, phosphorus sources, sulfur sources, inorganic ions, and organic nutrient sources as necessary.

For example, any carbon source may be used so far as the microbes can utilize it. Specific examples of the carbon source that can be used include sugars such as glucose, fructose, maltose and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic salts such as ammonium sulfate and ammonium chloride, ammonium salts of organic acids such as ammonium fumarate and ammonium citrate, nitrates such as sodium nitrate and potassium nitrate, organic nitrogen compounds such as peptone, yeast extract, meat extract and corn steep liquor as well as their mixtures.

In addition, ordinary nutrient sources used in media, such as inorganic salts, trace metal salts and vitamins, can also be suitably mixed and used.

There is no particular restriction on culturing conditions, and cultivation can be carried out, for example, for about 12 to about 48 hours while properly controlling the pH and temperature with a pH range of 5 to 8 and a temperature range of 15 to 40° C., respectively, under aerobic conditions.

(2-3) Enzyme Purification

As previously mentioned, the peptide-forming enzyme used in the present invention can be purified from bacteria belonging to, for example, the genus *Empedobacter*. A method for isolating and purifying a peptide-forming enzyme from *Empedobacter brevis* is explained as an example of purification of the enzyme.

First, a microbial cell extract is prepared from microbial cells of *Empedobacter brevis*, for example, the strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) by disrupting the cells using a physical method such as ultrasonic disruption or an enzymatic method using a cell wall-dissolving enzyme and removing the insoluble fraction by centrifugal separation and so forth. The peptide-producing enzyme can then be purified by fractionating the cell extract containing the enzyme obtained in the above manner by combining ordinary protein purification methods such as anion exchange chromatography, cation exchange chromatography or gel filtration chromatography.

An example of a carrier for use in anion exchange chromatography is Q-Sepharose HP (manufactured by Amersham). The enzyme is recovered in the non-adsorbed fraction under conditions of pH 8.5 when the cell extract containing the enzyme is applied to a column packed with the carrier.

An example of a carrier for use in cation exchange chromatography is MonoS HR (manufactured by Amersham). After adsorbing the enzyme onto the column by applying the cell extract containing the enzyme to a column packed with the carrier and then washing the column, the enzyme is eluted with a buffer solution containing a high salt concentration. At that time, the both methods that the salt concentration is step-wisely increased or is gradiently increased are available. For example, in the case of using MonoS HR, the enzyme adsorbed onto the column is eluted at an NaCl concentration of about 0.2 to about 0.5 M.

The enzyme purified in the manner described above can then be further purified with homogeneity by gel filtration chromatography and so forth. An example of the carrier for use in gel filtration chromatography is Sephadex 200 pg (manufactured by Amersham).

In the aforementioned purification procedure, the fraction containing the enzyme can be verified by assaying the peptide-forming activity of each fraction according to the method indicated in the examples to be described later. The internal amino acid sequence of the enzyme purified in the manner described above is shown in SEQ ID NO: 1 and SEQ ID NO: 2 of the Sequence Listing.

In addition, a preferable mode of the enzyme of the present invention is an enzyme having the property to be able to use both an amino acid ester and an amino acid amide as a substrate for the carboxy component. The words "both an amino acid ester and an amino acid amide can be used as a substrate" means that at least one or more types of amino acid ester and at least one or more types of amino acid amide can be used as a substrate. In addition, another preferable mode of the enzyme of the present invention is an enzyme having the property to be able to use all of a C-unprotected peptide being equal to or longer than a dipeptide, a C-protected peptide being equal to or longer than a dipeptide, and a peptide being equal to or longer than a dipeptide in which the C-terminal molecule is an amine instead of an amino acid as a substrate for the amine component. The words "the ability to use all of a C-unprotected peptide being equal to or longer than a dipeptide, a C-protected peptide being equal to or longer than a dipeptide, and a peptide being equal to or longer than a dipeptide in which the C-terminal molecule is an amine instead of an amino acid" mean that at least one or more types of a C-unprotected peptide being equal to or longer than a dipeptide, at least one or more types of a C-protected peptide being equal to or longer than a dipeptide, and at least one or more types of a peptide being equal to or longer than a dipeptide in which the C-terminal molecule is an amine instead of an amino acid can be used as a substrate. The enzyme of the present invention has a wide range of substrate specificity with respect to the carboxy component or the amino component. The properties are preferable in that a wide range of raw materials can be selected, which in turn is favorable in terms of cost and production equipment in the case of industrial production.

(2-4) Isolation of DNA, Construction of Transformant and Purification of Peptide-Forming Enzyme (2-4-1) Isolation of DNA The inventors of the present invention first succeeded in isolating one type of DNA encoding a peptide-forming enzyme that can be used in the peptide production method of the present invention from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). A DNA having a base sequence consisting of bases numbers 61 to 1908 of the base sequence described in SEQ ID NO: 5, which is a DNA of the present invention, was isolated from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). The DNA having the base sequence consisting of bases numbers 61 to 1908 is a code sequence (CDS) portion. In the base sequence consisting of bases numbers 61 to 1908 is contained a signal sequence region and a mature protein region. The signal sequence region consists of bases numbers 61 to 126, while the mature protein region consists of bases numbers 127 to 1908. That is, the present invention provides both a gene for a peptide enzyme protein that contains a signal sequence, and a gene for a peptide enzyme protein in the form of a mature protein. The signal sequence contained in the sequence described in SEQ ID NO: 5 is a kind of leader sequence. The main function of a leader peptide encoded by the leader sequence is presumed to be excretion from inside the cell membrane to outside the cell membrane. The protein encoded by bases numbers 127 to 1908, namely the site excluding the leader peptide, is a mature protein and exhibits a high activity of peptide-forming.

The DNA consisting of the base sequence that consists of bases numbers 61 to 1917 described in SEQ ID NO: 11, which is also a DNA of the present invention, was isolated from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). The DNA consisting of the base sequence that consists of bases numbers 61 to 1917 is a code sequence (CDS) portion. In the base sequence consisting of bases numbers 61 to 1917, a signal sequence region and a mature protein region are contained. The signal sequence region consists of bases numbers 61 to 120, while the mature protein region consists of bases numbers 121 to 1917. That is, the present invention provides both a gene for a peptide enzyme protein that contains a signal sequence, and a gene for a peptide enzyme protein in the form of a mature protein. The signal sequence contained in the sequence described in SEQ ID NO: 11 is a kind of leader sequence. The main function of a leader peptide encoded by the leader sequence is presumed to be excretion from inside the cell membrane to outside the cell membrane. The protein encoded by bases numbers 121 to 1917, namely the portion excluding the leader peptide, is a mature protein and exhibits a high activity of peptide-forming.

Furthermore, the various gene recombination techniques indicated below can be carried out in accordance with the descriptions in Molecular Cloning, 2nd edition, Cold Spring Harbor Press (1989) and other publications.

A DNA encoding an enzyme that can be used in the present invention can be obtained by polymerase chain reaction (PCR, refer to White, T J. et al., Trends Genet., 5, 185 (1989)) or hybridization from a chromosomal DNA or a DNA library of *Empedobacter brevis* or *Sphingobacterium* sp. Primers used in PCR can be designed based on the internal amino acid base sequences determined on the basis of purified peptide-forming enzyme as explained in the previous section (3). In addition, since the base sequences of the peptide-forming enzyme genes (SEQ ID NO: 5 and SEQ ID NO: 11) have been identified by the present invention, primers or hybridization probes can be designed on the basis of these base sequences, and the gene can be isolated using the probes. If primers having sequences corresponding to the 5'-nontranslated region and 3'-nontranslated region, respectively, are used as PCR primers, the full-length encoded region of the enzyme can be amplified. Taking as an example the case of amplifying a region containing both the leader sequence and a mature protein encoding region as described in SEQ ID NO: 5, specific examples of primers include a primer having a base sequence of the region upstream of base number 61 in SEQ ID NO: 5 for the 5'-side primer, and a primer having a sequence complementary to the base sequence of the region downstream of base number 1908 for the 3'-side primer.

Primers can be synthesized, for example, according to ordinary methods using the phosphoamidite method (refer to Tetrahedron Letters (1981), 22, 1859) by use of the Model 380B DNA Synthesizer manufactured by Applied Biosystems. The PCR reaction can be carried out, for example, by using the Gene Amp PCR System 9600 (Perkin-Elmer) and the Takara LA PCR In Vitro Cloning Kit (Takara Shuzo) in accordance with the method specified by the supplier such as the manufacturer.

A DNA that encodes an enzyme that can be used in the peptide production method of the present invention, regardless of whether the DNA contains a leader sequence or not, includes a DNA that is substantially identical to the DNA consisting of the CDS described in SEQ ID NO: 5 of the Sequence Listing. Namely, a DNA substantially identical to the DNA of the present invention can be obtained by isolating a DNA consisting of a base sequence complementary to the CDS described in SEQ ID NO: 5 of the Sequence Listing, or a DNA that hybridizes with a probe prepared from the same base sequence under stringent conditions and encodes a protein having peptide-forming activity, from a mutant DNA encoding the enzyme or cells that possess that DNA.

The DNA of the present invention, regardless of whether it contains a leader sequence or not, includes a DNA that is substantially identical to the DNA consisting of the CDS described in SEQ ID NO: 11 of the Sequence Listing. Namely, a DNA substantially identical to the DNA of the present invention can be obtained by isolating a DNA consisting of a base sequence complementary to the CDS described in SEQ ID NO: 11 of the Sequence Listing, or a DNA that hybridizes with a probe prepared from the same base sequence under stringent conditions and encodes a protein having peptide-forming activity, from a mutant DNA encoding the enzyme or cells that possess that DNA.

Namely, in the present invention, the DNA indicated in (a) to (h) below can be used:

(a) A DNA having a base sequence consisting of bases numbers 127 to 1908 of a base sequence described in SEQ ID NO: 5 of the Sequence Listing;

(b) A DNA that hybridizes with a DNA having a base sequence complementary to the base sequence consisting of bases numbers 127 to 1908 of the base sequence described in SEQ ID NO: 5 of the Sequence Listing under stringent conditions, and encodes a protein that has peptide-forming activity;

(c) A DNA having a base sequence consisting of bases numbers 121 to 1917 of a base sequence described in SEQ ID NO: 11 of the Sequence Listing;

(d) A DNA that hybridizes with a DNA having a base sequence complementary to the base sequence that consisting of bases numbers 121 to 1917 of the base sequence described in SEQ ID NO: 11 of the Sequence Listing under stringent conditions, and encodes a protein that has peptide-forming activity;

(e) A DNA having a base sequence consisting of bases numbers 61 to 1908 of a base sequence described in SEQ ID NO: 5 of the Sequence Listing;

(f) A DNA that hybridizes with a DNA having a base sequence complementary to the base sequence that consisting of bases numbers 61 to 1908 of the base sequence described in SEQ ID NO: 5 of the Sequence Listing under stringent conditions, and encodes a protein that has peptide-forming activity;

(g) A DNA having a base sequence consisting of bases numbers 61 to 1917 of a base sequence described in SEQ ID NO: 11 of the Sequence Listing;

(h) A DNA that hybridizes with a DNA having a base sequence complementary to the base sequence that consisting of bases numbers 61 to 1917 of the base sequence described in SEQ ID NO: 11 of the Sequence Listing under stringent conditions, and encodes a protein containing a mature protein region that has peptide-forming activity.

A probe can be produced in accordance with conventional methods based on, for example, the base sequence described in SEQ ID NO: 5 of the Sequence Listing. In addition, a method for isolating a target DNA by using a probe to find a DNA that hybridizes with the probe may also be carried out in accordance with conventional methods. For example, a DNA probe can be produced by amplifying a base sequence cloned in a plasmid or phage vector, cleaving the base sequence desired to be used as a probe with a restriction enzyme and then extracting the desired base sequence. The cleaving site can be adjusted depending on the target DNA.

The term "stringent conditions" as used herein refers to conditions under which a so-called specific hybrid is formed but no non-specific hybrid is formed. It is difficult to precisely express this condition in numerical values. For example, mention may be made of a condition under which DNAs having a high homology, for example, 50% or more, preferably 80% or more, more preferably 90% or more, hybridize with each other and DNAs having a lower homology than these do not hybridize with each other, or ordinary conditions for rinse in southern hybridization under which hybridization is performed at 60° C. in a salt concentration corresponding to 1×SSC and 0.1% SDS, preferably 0.1×SSC, and 0.1% SDS. Although the genes that hybridize under such conditions include genes in which a stop codon occurs at an intermediate site or which lose activity due to a mutation in the active center, these can be easily removed by assaying the enzyme activity of the expression product using a method to be described later after ligating them to a commercially available expression vector, expressing them in a suitable host.

However, in the case of a base sequence that hybridizes under stringent conditions as described above, it is preferable that the protein encoded by that base sequence retains about a half or more, preferably 80% or more, and more preferably 90% or more, of the enzyme activity of the protein having the amino acid sequence encoded by the original base sequence under conditions of 50° C. and pH 8. For example, when explained on the case of a base sequence that hybridizes under stringent conditions with a DNA that consists of a base sequence complementary to a base sequence that consists of bases numbers 127 to 1908 of the base sequence described in SEQ ID NO: 5, it is preferable that the protein encoded by that base sequence retains about a half or more, preferably 80% or more, and more preferably 90% or more, of the enzyme activity of the protein having an amino acid sequence that consists of amino acid residues numbers 23 to 616 of the amino acid sequence described in SEQ ID NO: 6 under conditions of 50° C. and pH 8.

An amino acid sequence encoded by the CDS described in SEQ ID NO: 5 of the Sequence Listing is shown in SEQ ID NO: 6 of the Sequence Listing. In addition, an amino acid sequence encoded by the CDS described in SEQ ID NO: 11 of the Sequence Listing is shown in SEQ ID NO: 12 of the Sequence Listing. The full-length amino acid sequence described in SEQ ID NO: 6 contains a leader peptide and a mature protein region, with amino acid residues numbers 1 to 22 constituting the leader peptide, and amino acid residues numbers 23 to 616 constituting the mature protein region. In addition, the full-length amino acid sequence described in SEQ ID NO: 11 includes a leader peptide and a mature protein region, with amino acid residues numbers 1 to 20 constituting the leader peptide, and amino acid residues 21 to 619 constituting the mature protein region.

The protein encoded by the DNA of the present invention is a protein in which the mature protein has peptide-forming activity, and a DNA that encodes a protein substantially identical to a protein having the amino acid sequence described in SEQ ID NO: 6 or SEQ ID NO: 12 of the Sequence Listing, regardless of whether it contains a leader peptide or not, is also included in the DNA of the present invention. (Note that, base sequences are specified from amino acid sequences in accordance with the codes of the universal codons.) Namely, the present invention provides DNAs that encode proteins indicated in (A) to (H):

(A) A protein having an amino acid sequence consisting of amino acid residues numbers 23 to 616 of an amino acid sequence described in SEQ ID NO: 6 of the Sequence Listing;

(B) A protein having an amino acid sequence including substitution, deletion, insertion, addition and/or inversion of one or a plurality of amino acids in the amino acid sequence consisting of amino acid residues numbers 23 to 616 of the amino acid sequence described in SEQ ID NO: 6 of the Sequence Listing, and having activity to form, from an amine component that is a peptide being equal to or longer than a dipeptide and a carboxy component, a peptide having one more peptide bond than the amine component;

(C) A protein having an amino acid sequence consisting of amino acid residues numbers 21 to 619 of the amino acid sequence described in SEQ ID NO: 12 of the Sequence Listing;

(D) A protein having an amino acid sequence including substitution, deletion, insertion, addition and/or inversion of one or a plurality of amino acids in the amino acid sequence consisting of amino acid residues numbers 21 to 619 of the amino acid sequence described in SEQ ID NO: 12 of the Sequence Listing, and having activity to form, from an amine component that is a peptide being equal to or longer than a dipeptide and a carboxy component, a peptide having one more peptide bond than the amine component;

(E) A protein having an amino acid sequence described in SEQ ID NO: 6 of the Sequence Listing;

(F) A protein containing a mature protein region, the protein having an amino acid sequence including substitution, deletion, insertion, addition and/or inversion of one or a plurality of amino acids in the amino acid sequence described in SEQ ID NO: 6 of the Sequence Listing, and having activity to form, from an amine component that i is a peptide being equal to or longer than a dipeptide and a carboxy component, a peptide having one more peptide bond than the amine component;

(G) A protein having an amino acid sequence described in SEQ ID NO: 12 of the Sequence Listing; and, (H) A protein containing a mature protein region, the protein having an amino acid sequence including substitution, deletion, insertion, addition and/or inversion of one or a plurality of amino acids in the amino acid sequence described in SEQ ID NO: 12 of the Sequence Listing, and having activity to form, from an amine component that i is a peptide being equal to or longer than a dipeptide and a carboxy component, a peptide having one more peptide bond than the amine component.

In the peptide production method of the present invention, one type or two or more types of protein selected from the group consisting of proteins encoded by the DNAs indicated in (a) to (h) above and the group consisting of proteins indicated in (A) to (H) above can be used.

Here, the term "a plurality of", which may vary depending on the locations in the three-dimensional structure of the protein of and types of the amino acid residues, means 2 to 100, preferably 2 to 50 and more preferably 2 to 10. However, in the case of amino acid sequences of the proteins of (B), (D), (F) and (H) containing therein substitution, deletion, insertion, addition and/or inversion of one or a plurality of amino acid residues, it is preferable that the proteins retain about a half or more, more preferably 80% or more, and even more preferably 90% or more of the enzyme activity in comparison with the activity of proteins that contain no mutation under conditions of 50° C. and pH 8. For example, in explaining this on the case of (B), it is preferable that the protein having the amino acid sequence described in SEQ ID NO: 6 of the Sequence Listing of (B) but contains substitution, deletion, insertion, addition or inversion of one or a plurality of amino acid residues therein retains about a half or more, more preferably 80% or more, and even more preferably 90% or more of the enzyme activity of the protein having the amino acid sequence described in SEQ ID NO: 6 of the Sequence Listing under conditions of 50° C. and pH 8.

A mutation of an amino acid such as those indicated in the aforementioned (B) is obtained by modifying the base sequence of the gene of the enzyme of the present invention so that amino acids of the enzyme gene in specific sites are substituted, deleted, inserted or added. In addition, modified DNAs such as those described above can also be obtained by conventionally known mutagenesis treatments. Mutagenesis treatments include, for example, a method in which a DNA that encodes the enzyme is treated in vitro with hydroxylamine or the like, as well as a method in which bacteria belonging to the genus *Escherichia* that possess a DNA encoding the enzyme are treated by a mutagen normally used in artificial mutagenesis, such as ultraviolet irradiation, N-methyl-N'-nitro-N-nitrosoguanidine (NTG) or nitrous acid.

In addition, the base substitution, deletion, insertion, addition and/or inversion described above also include naturally-occurring mutations such as differences attributable to a microbe species or strain. By expressing a DNA having such a mutation in suitable cells and examining the enzyme activity of the expression product, a DNA can be obtained that encodes the protein described in SEQ ID NO: 6 or 12 of the Sequence Listing or a protein substantially identical thereto.

(2-4-2) Construction of Transformants and Production of Peptide-Forming Enzymes

A peptide-forming enzyme that can be used in the peptide production method of the present invention can be produced by introducing the DNA explained in the aforementioned section (2-4-1) into a suitable host and expressing within that host.

With respect to hosts for expressing a protein encoded by the DNA, examples of the hosts that can be used include various prokaryotic cells including bacteria belonging to the genus *Escherichia* such as *Escherichia coli*, *Empedobacter*, *Sphingobacterium*, *Flavobacterium* and *Bacillus subtilis*, as well as various eukaryotic cells including *Saccharomyces cerevisiae*, *Pichia stipitis* and *Aspergillus oryzae*.

A recombinant DNA used to introduce a DNA into a host can be prepared by inserting the DNA to be introduced into a vector corresponding to the type of host in which the DNA is to be expressed, in such a form that the protein encoded by that DNA can be expressed. If a promoter that is originally associated with the gene encoding the peptide-forming enzyme in, e.g., *Empedobacter brevis* is capable of working in the host cells, such a promoter can be used as the promoter for expressing the DNA in the present invention. If necessary, another promoter that is capable of working in the host cells may be connected to the DNA of the present invention, for expressing the DNA under the control of the promoter.

Examples of transformation methods for introducing a recombinant DNA into host cells include the method of D. M. Morrison (see Methods in Enzymology, 68, 326 (1979)) or the method in which DNA permeability is increased by treating receptor microbial cells with calcium chloride (see Mandel, H. and Higa, A., J. Mol. Biol., 53, 159 (1970)).

In the case of mass production of a protein using recombinant DNA technology, conjugating the protein within a transformant that produces the protein to form an inclusion body of protein is also a preferable mode for carrying out the present invention. Advantages of this expression and production method include protection of the target protein from digestion by proteases present within the microbial cells, and simple and easy purification of the target protein by disrupting the microbial cells followed by centrifugal separation and so forth.

The inclusion body of protein obtained in this manner is solubilized with a protein denaturant and the protein is converted to a properly folded, physiologically active protein through an activity regeneration procedure that consists primarily of removal of the denaturant. There are numerous examples of this, including regeneration of the activity of human interleukin-2 (see Japanese Patent Application Laid-open Publication No. S61-257931).

To obtain an active protein from inclusion bodies, a series of procedures including solubilization and activity regeneration are required, and the procedure is more complex than the case of producing the active protein directly. However, in the case of producing a protein that has a detrimental effect on microbial growth in large volumes within microbial cells, that effect can be suppressed by accumulating the proteins in the form of inclusion bodies of protein that are inactive in the microbial cells.

Examples of mass production methods for producing a target protein in the form of inclusion bodies include a method in which a target protein is expressed independently under the control of a powerful promoter, and a method in which a target protein is expressed in the form of a fused protein with a protein that is known to be expressed in a large volume.

Hereinafter, the present invention will be explained more specifically taking as an example a method for producing transformed *Escherichia coli* and using that transformed microbe to produce a peptide-forming enzyme. Furthermore, in the case of producing peptide-forming enzyme in a microbe such as *Escherichia coli*, a DNA that encodes a precursor protein containing a leader sequence may be used or a DNA that consists only of a mature protein region that does not contain a leader sequence may be used, and the DNA can be suitably selected for the protein encoding sequence depending on the production conditions, form, usage conditions and so forth of the enzyme to be produced.

Promoters normally used in the production of heterogeneous proteins in *Escherichia coli* can be used as a promoter for expressing a DNA encoding a peptide-forming enzyme. Examples of such promoters include T7 promoter, lac promoter, trp promoter, trc promoter, tac promoter, lambda phage PR promoter, PL promoter and other powerful promoters. In addition, examples of vectors that can be used include pUC19, pUC18, pBR322, pHSG299, pHSG298, pHSG399, pHSG398, RSF1010, pMW119, pMW118, pMW219, and pMW218. Besides, vectors of phage DNA can also be used. Moreover, expression vectors that contain promoters and are capable of expressing an inserted DNA sequence can be used.

To produce peptide-forming enzyme in the form of a fused protein inclusion body, a gene that encodes another protein, and preferably a hydrophilic peptide, is ligated upstream or downstream of the peptide-forming enzyme gene. The gene that encodes another protein in this manner may be any gene that increases the amount of the fused protein accumulated and enhances the solubility of the fused protein after the denaturation and regeneration steps. Examples of candidates for such genes include T7 gene 10, β-galactosidase gene, dehydrofolate reductase gene, γ-interferon gene, interleukin-2 gene and prochymosin gene.

When these genes are ligated to the genes that encode peptide-forming enzymes, the genes are ligated so that reading frames of codons are consistent. It is recommended that the genes be ligated at a proper restriction enzyme site or a synthetic DNA having a proper sequence be utilized.

Further, to increase a production amount of the peptide-forming enzyme, it is preferable in some cases that a terminator, which is a transcription terminating sequence, be ligated to downstream of the fusion protein gene. The terminator includes, for example, a T7 terminator, an fd phage terminator, a T4 terminator, a tetracycline resistant gene terminator, and an *Escherichia coli* trpA gene terminator.

As the vectors for introducing a gene that encodes a peptide-forming enzyme or a fused protein between the peptide-forming enzyme and another protein in *Escherichia coli* are preferred so-called multi-copy type vectors, examples of which include a plasmid having a replicator derived from ColE1, such as a pUC-based plasmid, and a pBR322-based plasmid or derivatives thereof. The "derivatives" as used herein refer to those plasmids that are subjected to modification by substitution, deletion, insertion, addition and/or inversion of bases. Note that the modification as used herein includes modifications by a mutagenesis treatment with a mutagen or UV irradiation, or modifications by spontaneous mutation.

To screen transformants, it is preferable that the vectors have markers such as an ampicillin resistant gene. These plasmids are commercially available expression vectors having potent promoters (a pUC-based vector (manufactured by Takara Shuzo, Co., Ltd.), such as pRROK-based vector (manufactured by Clonetech Laboratories, Inc.), pKK233-2 (manufactured by Clonetech Laboratories, Inc.) and so forth.

A recombinant DNA is obtained by ligating a DNA fragment to a vector DNA. In this case, a promoter, a gene encoding the peptide-forming enzyme or a fused protein consisting of the peptide-forming enzyme and another protein, and depending on the case, a terminator are ligated in that order.

When *Escherichia coli* is transformed using the recombinant DNA and the resulting *Escherichia coli* is cultured, a peptide-forming enzyme or a fused protein consisting of the peptide-forming enzyme and another protein is expressed and produced. Although a strain that is normally used in the expression of a heterogeneous gene can be used as a host to be transformed, *Escherichia coli* JM109, for example, is preferable. Methods for transformation and methods for selection from transformants are described in Molecular Cloning, 2nd Edition, Cold Spring Harbor Press (1989) and other publications.

In the case of expressing a peptide-forming enzyme in the form of a fusion protein, the peptide-forming enzyme may be cleaved out using a restriction protease that uses a sequence not present in the peptide-forming enzyme, such as blood coagulation factor Xa or kallikrein, as the recognition sequence.

A medium normally used for culturing *Escherichia coli*, such as M9-casamino acid medium or LB medium, may be used as a production medium. In addition, culturing conditions and induction conditions for production are suitably selected according to a variety of the marker of the vector, promoter, type of host microbe and so forth.

The following method can be used to recover the peptide-forming enzyme or fused protein consisting of the peptide-forming enzyme and another protein. If the peptide-forming enzyme or its fused protein was produced as solubilized form within the microbial cells, after recovering the microbial cells, the microbial cells are disrupted or lysed so that they can be used as a crude enzyme liquid. Moreover, the peptide-forming enzyme or its fused protein can be purified prior to use by ordinary techniques such as precipitation, filtration or column chromatography as necessary. In this case, a purification method using an antibody of the peptide-forming enzyme or its fused protein can also be used.

In the case where protein inclusion bodies are formed, the inclusion bodies are solubilized with a denaturant. They may be solubilized together with the microbial cell protein. However, in consideration of the following purification procedure, the inclusion bodies are preferably taken out and then solubilized. Conventionally known methods may be used to recover the inclusion bodies from the microbial cells. For example, inclusion bodies can be recovered by disrupting the microbial cells followed by centrifugal separation. Examples of denaturants capable of solubilizing inclusion bodies include guanidine hydrochloride (for example, 6 M, pH 5 to 8) and urea (for example, 8 M).

A protein having activity is regenerated by removing these denaturants by dialysis. A Tris-HCl buffer solution or a phosphate buffer solution and so forth may be used as solution used in dialysis, and the concentration may be, for example, 20 mM to 0.5 M, while the pH may be, for example, 5 to 8.

The protein concentration during the regeneration step is preferably held to about 500 µg/ml or less. The dialysis temperature is preferably 5° C. or lower to inhibit the regenerated peptide-forming enzyme from undergoing self-crosslinking. Moreover, in addition to dialysis, dilution or ultrafiltration may be used to remove the denaturants, and it is expected that the activity can be regenerated regardless of whichever denaturant is used.

Hereinafter, the present invention will be explained by examples. However, the present invention is not limited to these examples. In addition to confirmation by ninhydrin coloring of thin-film chromatograms (qualitative), quantitative determinations were made by the following high-performance liquid chromatography in order to assay products. Column: InertsiL ODS-2 (manufactured by GL Science, Inc.), eluate: aqueous phosphate solution containing 5.0 mM sodium 1-octanesulfonate (pH 2.1):methanol=100:15 to 50, flow rate: 1.0 mL/min, detection: 210 nanometers (nm).

EXAMPLES

Example 1

Cultivation of Microbe (*Empedobacter brevis* FERM BP-8113)

A 50 mL medium (pH 6.2) containing 5 grams (g) glucose, 5 g ammonium sulfate, 1 g monopotassium phosphate, 3 g dipotassium phosphate, 0.5 g magnesium sulfate, 10 g yeast extract and 10 g peptone in 1 liter (L) was transferred to a 500 mL Sakaguchi flask and sterilized at 115° C. for 15 minutes. This medium was then inoculated with one loopful cells of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) that had been cultured at 30° C. for 16 hours in the same medium, followed by shake culturing at 30° C. for 16 hours and 120 strokes/min.

Example 2

Production of Peptide Using Microbial Cells

Microbial cells were collected by centrifuging (10,000 rounds per minute (rpm), 15 minutes) the culture broth obtained in Example 1 followed by suspending to a concentration of 100 g/L in 100 mM borate buffer (pH 9.0) containing 10 mM EDTA. After respectively adding 1 mL of this suspension to 1 mL of 100 mM borate buffer (pH 9.0) containing 10 mM EDTA, 200 mM of the following carboxy components and 400 mM of the following amino acids to bring to a final volume of 2 mL, the reaction was carried out at 18° C. for 2 hours. The peptides that were formed as a result of this reaction are shown in Table 1.

Example 3

Purification of Enzyme

The procedure after centrifugal separation was carried out either on ice or at 4° C. *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultivated in the same manner in as Example 1, and the microbial cells were collected by centrifugal separation (10,000 rpm, 15 minutes). After washing 16 g of microbial cells with 50 mM Tris-HCl buffer (pH 8.0), they were suspended in 40 milliliters (ml or mL) of the same buffer and subjected to ultrasonic disrupting treatment for 45 minutes at 195 watts. This sonicate was then centrifuged (10,000 rpm, 30 minutes) to remove the cell debris and obtain an ultrasonically disrupted liquid supernatant. This ultrasonically disrupted liquid supernatant was dialyzed overnight against 50 mM Tris-HCl buffer (pH 8.0) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 8.0), and the active fraction was collected from the non-adsorbed fraction. This active fraction was dialyzed overnight against 50 mM acetate buffer (pH 4.5) followed by removal of the insoluble fraction by centrifugal separation (10,000 rpm, 30 minutes) to obtain a dialyzed fraction in the form of the supernatant liquid. This dialyzed fraction was then applied to a Mono S column (manufactured by Amersham) pre-equilibrated with 50 mM acetate buffer (pH 4.5) to elute enzyme with a linear concentration gradient of the same buffer containing 0 to 1 M NaCl. The fraction that had the lowest level of contaminating protein among the active fractions was applied to a Superdex 200 pg column (manufactured by Amersham) pre-equilibrated with 50 mM acetate buffer (pH 4.5) containing 1 M NaCl, and gel filtration was performed by allowing the same buffer (pH 4.5) containing 1 M NaCl to flow through the column to obtain an active fraction solution. As a result of performing these procedures, the peptide-forming enzyme used in the present invention was confirmed to have been purified with homogeneity based on the experimental results of electrophoresis. The enzyme recovery rate in the aforementioned purification process was 12.2% and the degree of purification was 707 folds.

TABLE 1

| Carboxy component | Amine component | Formed peptide | (mM) | Carboxy component | Amine component | Formed peptide | (mM) |
|---|---|---|---|---|---|---|---|
| L-Ala-OMe | L-Leu | L-Ala-L-Leu | 38.2 | Gly-OMe | L-His | L-Gly-L-His | 22.1 |
|  | L-Met | L-Ala-L-Met | 68.3 | L-Ser-OMe | L-Ser | L-Ser-L-Ser | 29.0 |
|  | L-Phe | L-Ala-L-Phe | 62.4 | L-Val-OMe | L-Met | L-Val-L-Met | 10.5 |
|  | L-Ser | L-Ala-L-Ser | 51.3 | L-Met-OMe | L-Phe | L-Met-L-Phe | 28.5 |
|  | L-His | L-Ala-L-His | 52.1 | L-Thr-OMe | L-Leu | L-Thr-L-Leu | 23.0 |
|  | L-Arg | L-Ala-L-Arg | 72.1 | L-Ile-OMe | L-Met | L-Ile-L-Met | 8.3 |
|  | L-Gln | L-Ala-L-Gln | 68.0 |  |  |  |  |

(Hydrochloride salts were used for all the carboxy components.)

Example 4

Measurement of Molecular Weight of Enzyme (SDS-Gel Electrophoresis)

A 0.3 microgram (μg) equivalent of the purified enzyme fraction obtained by the method of Example 3 was applied to polyacrylamide electrophoresis. 0.3% (w/v) Tris, 1.44% (w/v) glycine and 0.1% (w/v) sodium laurylsulfate were used for the electrophoresis buffer solution, a gel having a concentration gradient of 10 to 20% (Multigel 10 to 20, manufactured by Daiichi Pure Chemicals) was used for the polyacrylamide gel, and Pharmacia molecular weight markers were used for the molecular weight markers. Following completion of electrophoresis, the gel was stained with Coomassie brilliant blue R-250, and a homogeneous band was detected at the location of a molecular weight of about 75 kilodalton (kDa).

(Gel Filtration)

The purified enzyme fraction obtained by the method of Example 3 was applied to a Superdex 200 pg column (manufactured by Amersham) pre-equilibrated with 50 mM acetate buffer (pH 4.5) containing 1 M NaCl, and gel filtration was carried out by allowing the same buffer (pH 4.5) containing 1 M NaCl to flow through the column to measure the molecular weight. Pharmacia molecular weight markers were used as standard proteins having known molecular weights to prepare a calibration curve. As a result, the molecular weight of the enzyme was about 150 kDa.

Based on the results of SDS-gel electrophoresis and gel filtration, the enzyme was suggested to be a homodimer having a molecular weight of about 75 kDa.

Example 5

Optimum pH of Enzyme

The effects of pH for L-alanyl-L-glutamine production from L-alanine methyl ester hydrochloride and L-glutamine were examined. Acetate buffer (pH 3.9 to 5.4), MES buffer (pH 5.4 to 6.4), phosphate buffer (pH 6.0 to 7.9), borate buffer (pH 7.8 to 9.3), CAPS buffer (pH 9.3 to 10.7) and $K_2HPO_4$—NaOH buffer (pH 10.8 to 11.6) were used as buffers. 1 microliter (μl) of the Mono S fraction enzyme obtained in Example 3 (about 180 U/ml) was added to 100 μl of 100 mM each buffer containing 100 mM L-alanine methyl ester, 200 mM L-glutamine and 10 mM EDTA and allowed to react at 18° C. for 5 minutes to measure the effects of pH on the reaction. The results based on assigning a value of 100% to the case of using borate buffer (pH 9.3) are shown in FIG. 1. As a result, the optimum enzyme pH was 8 to 9.5.

Example 6

Optimum Temperature of Enzyme

Figure 2:
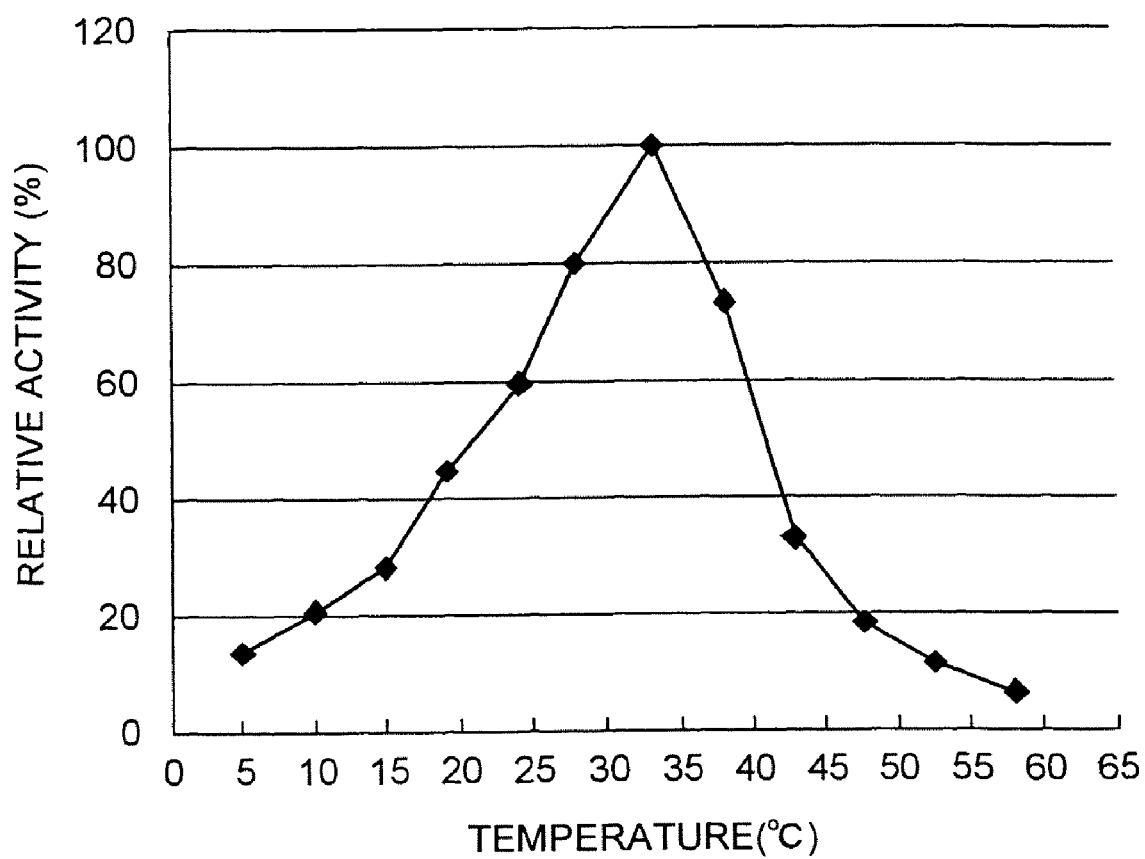
FIG. 2 shows the optimum temperature of an enzyme of *Empedobacter*.

The effects of temperature for L-alanyl-L-glutamine production from L-alanine methyl ester hydrochloride and L-glutamine were examined. 1 μl of the same enzyme fraction used in Example 5 was added to 100 μl of 100 mM borate buffer (pH 9.0) containing 100 mM L-alanine methyl ester, 200 mM L-glutamine and 10 mM EDTA and allowed to react for 5 minutes at each temperature to measure the effects of temperature on the reaction. The results based on assigning a value of 100% to the activity at 34° C. are shown in FIG. 2. As a result, the optimum enzyme temperature was 30 to 40° C.

Example 7

Enzyme Inhibitors

The effects of inhibitors on L-alanyl-L-glutamine production were examined using L-alanine methyl ester hydrochloride and L-glutamine as substrates. 2 μl of the same enzyme fraction used in Example 5 was added to 50 μl of 100 mM borate buffer (pH 9.0) containing 10 mM each of the enzyme inhibitors shown in Table 2, and allowed to react at 25° C. for 5 minutes. Note that, o-phenanthroline, phenylmethylsulfonyl fluoride and p-nitrophenyl-p'-guanidinobenzoate were dissolved in methanol to a concentration of 50 mM before use. The enzyme activity under each condition was indicated as the relative activity in the case of assigning a value of 100 to the production of L-alanyl-L-glutamine in the absence of enzyme inhibitor. Those results are shown in Table 2. As a result, among the serine enzyme inhibitors tested, the enzyme was not inhibited by phenylmethylsulfonyl fluoride, but it was inhibited by p-nitrophenyl-p'-guanidinobenzoate.

TABLE 2

|  | Enzyme inhibitor | Relative activity of L-Ala-L-Gln production (%) |
|---|---|---|
|  | None | 100 |
| Metal enzyme inhibitor | EDTA | 96 |
|  | o-Phenanthroline | 96 |
| SH enzyme inhibitor | N-Ethyl maleimide | 110 |
|  | Monoiodoacetate | 101 |
| Serine enzyme inhibitor | Phenylmethylsulfonyl Fluoride | 115 |
|  | 4-(2-Aminoethyl)benzene sulfonyl fluoride | 75 |
|  | p-Nitrophenyl-p'-guanidino benzoate | 0.1 |

Example 8

L-Alanyl-L-Glutamine Production from L-Alanine Methyl Ester and L-Glutamine

Figure 3:
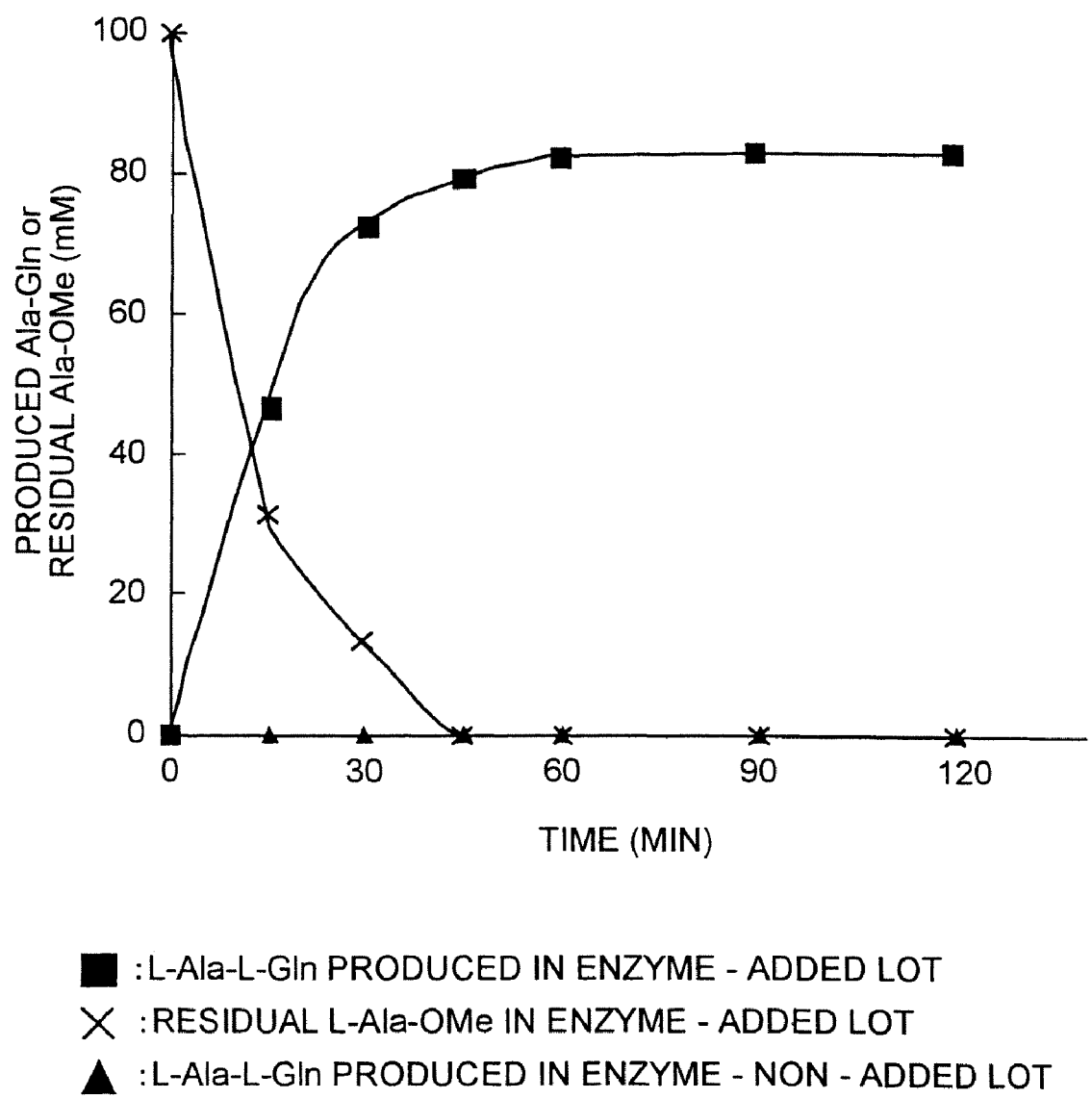
FIG. 3 shows the time course of L-alanyl-L-glutamine production from L-alanine methyl ester and L-glutamine.

3 μl of the same enzyme fraction as used in Example 5 was added to 100 μl of 100 mM borate buffer (pH 9.0) containing 100 mM L-alanine methyl ester hydrochloride, 200 mM L-glutamine and 10 mM EDTA, and allowed to react at 18° C. As a result, as shown in FIG. 3, 83 mM L-alanyl-L-glutamine (L-Ala-L-Gln) was formed in the case of an enzyme-added lot, and the concentration of by-product L-Ala-L-Ala-L-Gln was 1.3 mM. On the other hand, there was scarcely any production of L-Ala-L-Gln observed in an enzyme-non-added lot, and L-Ala-L-Gln production was only about 0.07 mM after reaction for 120 minutes.

Example 9

Effects of L-Glutamine Concentration on L-Alanyl-L-Glutamine Production

1 μl of the same enzyme fraction as used in Example 5 was added to 100 μl of 100 mM borate buffer (pH 9.0) containing 100 mM L-alanine methyl ester hydrochloride, L-glutamine at the concentrations shown in Table 3 and 10 mM EDTA, and allowed to react at 18° C. for 2 hours. Those results are shown in Table 3.

TABLE 3

| L-Alanine methyl ester hydrochloride (mM) | L-Glutamine (mM) | L-Ala-L-Gln (mM) |
|---|---|---|
| 100 | 100 | 68.2 |
|  | 110 | 72.1 |
|  | 120 | 73.3 |
|  | 130 | 75.1 |
|  | 150 | 75.5 |
|  | 200 | 82.0 |

Example 10

Substrate Specificity of Enzyme (1)

Ester specificity was examined in the case of using L-amino acid ester as the carboxy component. 2 μl of the same enzyme fraction as used in Example 5 was added to 100 μl of 100 mM borate buffer (pH 9.0) containing the 100 mM carboxy components indicated in Table 4, 200 mM L-glutamine and 10 mM EDTA, and allowed to react at 25° C. for 2 hours. The amounts of L-Ala-L-Gln formed in this reaction are shown in Table 4 (HCl represents hydrochloride in Table 4).

TABLE 4

| Carboxy component | L-Ala-L-Gln formed (mM) |
|---|---|
| L-Alanine methyl ester•HCl | 84.3 |
| L-Alanine ethyl ester•HCl | 91.5 |
| L-Alanine isopropyl ester•HCl | 78.9 |
| L-Alanine-t-butyl ester•HCl | 7.5 |

Example 11

Substrate Specificity of Enzyme (2)

Peptide production by using L-alanine methyl ester as the carboxy component and various L-amino acids as the amine component was examined. 2 μl of the same enzyme fraction as used in Example 5 was added to 100 μl of 100 mM borate buffer (pH 9.0) containing 100 mM L-alanine methyl ester hydrochloride, the 150 mM L-amino acids shown in Table 5 and 10 mM EDTA, and allowed to react at 25° C. for 3 hours. The amounts of each peptide formed in this reaction are shown in Table 5. (The "+" mark indicates that peptides production was confirmed but were unable to be quantified due to the absence of a standard, while "tr" indicates a trace amount.)

TABLE 5

| Amine component | Formed peptide (mM) | Amine component | Formed peptide (mM) |
|---|---|---|---|
| Gly | L-Ala-Gly 13.7 | L-Asn | L-Ala-L-Asn 65.5 |
| L-Ala | L-Ala-L-Ala 25.4 | L-Gln | L-Ala-L-Gln 79.3 |
| L-Val | L-Ala-L-Val 20.8 | L-Tyr | L-Ala-L-Tyr 17.6 |
| L-Leu | L-Ala-L-Leu 45.3 | L-CySH | L-Ala-L-CySH + |
| L-Ile | L-Ala-L-Ile 33.9 | L-Lys | L-Ala-L-Lys 71.8 |
| L-Met | L-Ala-L-Met 83.3 | L-Arg | L-Ala-L-Arg 88.0 |
| L-Phe | L-Ala-L-Phe 74.4 | L-His | L-Ala-L-His 66.9 |
| L-Trp | L-Ala-L-Trp 53.9 | L-Asp | L-Ala-L-Asp 2.1 |
| L-Ser | L-Ala-L-Ser 62.5 | L-Glu | L-Ala-L-Glu 42.9 |
| L-Thr | L-Ala-L-Thr 53.9 | L-Pro | L-Ala-L-Pro tr |

Example 12

Substrate Specificity of Enzyme (3)

Peptide production by using various types of L-amino acid methyl esters as the carboxy component and L-glutamine as the amine component was examined. 2 μl of the same enzyme fraction as used in Example 5 was added to 100 μl of 100 mM borate buffer (pH 9.0) containing 100 mM L-amino acid methyl ester hydrochlorides (AA-OMe.HCl) shown in Table 6, 150 mM L-glutamine and 10 mM EDTA, and allowed to react at 25° C. for 3 hours. The amounts of each of the peptides formed in this reaction are shown in Table 6. (The "+" mark indicates that peptides production was confirmed but were unable to be quantified due to the absence of a standard, while "tr" indicates a trace amount.) Furthermore, Tween-80 was added to the reaction system to a final concentration of 0.1% in the case of using L-Trp-OMe and L-Tyr-OMe.

TABLE 6

| Carboxy component | Formed peptide (mM) | Carboxy component | Formed peptide (mM) |
|---|---|---|---|
| Gly-OMe | Gly-L-Gln 54.7 | L-Tyr-OMe | L-Tyr-L-Gln 3.4 |
| L-Ala-OMe | L-Ala-L-Gln 74.6 | CySH-OMe | L-CySH-L-Gln + |
| L-Val-OMe | L-Val-L-Gln 15.4 | L-Lys-OMe | L-Lys-L-Gln + |
| L-Leu-OMe | L-Leu-L-Gln + | L-Arg-OMe | L-Arg-L-Gln 7.1 |
| L-Ile-OMe | L-Ile-L-Gln 8.4 | L-His-OMe | L-His-L-Gln + |
| L-Met-OMe | L-Met-L-Gln 12.0 | L-Asp-α-OMe | α-L-Asp-L-Gln tr |
| L-Phe-OMe | L-Phe-L-Gln 0.9 | L-Asp-β-OMe | β-L-Asp-L-Gln tr |
| L-Trp-OMe | L-Trp-L-Gln + | L-Glu-α-OMe | α-L-Glu-L-Gln + |
| L-Ser-OMe | L-Ser-L-Gln 24.0 | L-Glu-γ-OMe | γ-L-Glu-L-Gln + |
| L-Thr-OMe | L-Thr-L-Gln 81.9 | L-Pro-OMe | L-Pro-L-Gln 2.2 |
| L-Asn-OMe | L-Asn-L-Gln + |  |  |
| L-Gln-OMe | L-Gln-L-Gln 0.3 |  |  |

(Hydrochloride salts were used for all of the carboxy components.)

Example 13

Substrate Specificity of Enzyme (4)

Peptide production by using various L-amino acid methyl esters as the carboxy component and various L-amino acids as the amine component was examined. 2 μl of the same enzyme fraction as used in Example 5 was added to 100 μl of 100 mM borate buffer (pH 9.0) containing 100 mM L-amino acid methyl ester hydrochlorides (AA-OMe.HCl) shown in Table 7, 150 mM L-amino acids shown in Table 7 and 10 mM EDTA, and allowed to react at 25° C. for 3 hours. The amounts formed of each of the peptides formed in this reaction are shown in Table 7. (The "tr" indicates a trace amount.) Furthermore, Tween-80 was added to the reaction system to a final concentration of 0.1% in the case of using L-Trp-OMe. (The "+" mark indicates that peptides production was confirmed but were unable to be quantified due to the absence of a standard.)

TABLE 7

| Carboxy component | Amine component | Formed peptide | (mM) | Carboxy component | Amine component | Formed peptide | (mM) |
|---|---|---|---|---|---|---|---|
| Gly-OMe | L-CySH | Gly-L-CySH | 45.6 | L-Met-OMe | L-Ser | L-Met-L-Ser | 12.8 |
| | L-Arg | Gly-L-Arg | 25.5 | | L-Met | L-Met-L-Met | 25.0 |
| | L-Phe | Gly-L-Phe | 44.0 | | L-Phe | L-Met-L-Phe | 34.0 |
| | L-His | Gly-L-His | 31.6 | L-Ile-OMe | L-Ser | L-Ile-L-Ser | 17.2 |
| | L-Lys | Gly-L-Lys | 9.8 | | L-Met | L-Ile-L-Met | 10.0 |
| | L-Ser | Gly-L-Ser | 44.2 | | L-Phe | L-Ile-L-Phe | 5.2 |
| L-Thr-OMe | Gly | L-Thr-Gly | 9.4 | L-Arg-OMe | L-Ser | L-Arg-L-Ser | 3.6 |
| | L-Ala | L-Thr-L-Ala | 9.4 | | L-Met | L-Arg-L-Met | 0.7 |
| | L-Val | L-Thr-L-Val | 0.7 | | L-Phe | L-Arg-L-Phe | 1.9 |
| | L-Leu | L-Thr-L-Leu | 28.4 | L-Leu-OMe | L-Met | L-Leu-L-Met | 12.2 |
| | L-Met | L-Thr-L-Met | 38.6 | L-Trp-OMe | L-Met | L-Trp-L-Met | 4.1 |
| | L-Ser | L-Thr-L-Ser | 58.2 | L-Lys-OMe | L-Met | L-Lys-L-Met | 6.8 |
| L-Ser-OMe | L-Ser | L-Ser-L-Ser | 38.0 | L-His-OMe | L-Met | L-His-L-Met | 6.5 |
| | L-Met | L-Ser-L-Met | 12.5 | L-Asn-OMe | L-Glu | LAsn-L-Glu | 10.2 |
| | L-Phe | L-Ser-L-Phe | 20.3 | | | | |
| L-Val-OMe | L-Ser | L-Val-L-Ser | 30.8 | | | | |
| | L-Met | L-Val-L-Met | 10.3 | | | | |
| | L-Phe | L-Val-L-Phe | 6.1 | | | | |

(Hydrochloride salts were used for all of the carboxy components.)

Example 14

Substrate Specificity of Enzyme (5)

Peptide production by using L or D forms of various amino acid methyl esters as the carboxy component and L or D forms of various amino acids as the amine component was examined. 2 μl of the same enzyme fraction as used in Example 5 was added to 100 μl of 100 mM borate buffer (pH 9.0) containing 100 mM various amino acid methyl ester hydrochlorides (AA-OMe.HCl) shown in Table 8, 150 mM various amino acids shown in Table 8 and 10 mM EDTA, and allowed to react at 25° C. for 3 hours. The amounts of each of the peptides formed in this reaction are shown in Table 8. (The "tr" indicates a trace amount.)

TABLE 8

| Carboxy component | Amine component | Formed peptide (mM) | |
|---|---|---|---|
| D-Ala-OMe | L-Gln | D-Ala-L-Gln | 69.3 |
| D-Ala-OMe | L-Ser | D-Ala-L-Ser | 20.3 |
| D-Thr-OMe | | D-Thr-L-Ser | 1.0 |
| D-Ser-OMe | | D-Ser-L-Ser | 3.3 |
| D-Val-OMe | | D-Val-L-Ser | 0.6 |
| D-Met-OMe | | D-Met-L-Ser | 5.1 |
| L-Ala-OMe | D-Gln | L-Ala-D-Gln | 0.3 |
| L-Ala-OMe | D-Ser | L-Ala-D-Ser | 5.4 |
| L-Thr-OMe | | L-Thr-D-Ser | 6.9 |
| L-Ser-OMe | | L-Ser-D-Ser | 16.2 |
| L-Val-OMe | | L-Val-D-Ser | 1.4 |
| L-Met-OMe | | L-Met-D-Ser | 1.9 |
| D-Ala-OMe | D-Gln | D-Ala-D-Gln | tr |
| D-Ala-OMe | D-Ser | D-Ala-D-Ser | 0.2 |
| D-Thr-OMe | | D-Thr-D-Ser | 1.1 |
| D-Ser-OMe | | D-Ser-D-Ser | 2.5 |
| D-Val-OMe | | D-Val-D-Ser | 0.5 |
| D-Met-OMe | | D-Met-D-Ser | 2.7 |

(Hydrochloride salts were used for all of the carboxy components.)

Example 15

Substrate Specificity of Enzyme (6)

Peptide production by using various L-amino acid amides as the carboxy component, and various L-amino acids as the amine component was examined. 2 μl of the same enzyme fraction as that used in Example 5 was added to 100 μl of 100 mM borate buffer (pH 9.0) containing 100 mM L-amino acid amide hydrochlorides (AA-NH₂—HCl) shown in Table 9, 150 mM L-amino acids shown in Table 9 and 10 mM EDTA, and allowed to react at 25° C. for 3 hours. The amounts of each of the peptides formed in this reaction are shown in Table 9.

TABLE 9

| Carboxy component | Amine component | Formed Peptide (mM) | |
|---|---|---|---|
| L-Phe-NH₂ | L-Gln | L-Phe-L-Gln | 0.2 |
| L-Phe-NH₂ | L-Ser | L-Phe-L-Ser | 0.6 |
| L-Ala-NH₂ | L-Gln | L-Ala-L-Gln | 7.6 |
| L-Ala-NH₂ | L-Met | L-Ala-L-Met | 3.4 |
| L-Ala-NH₂ | L-His | L-Ala-L-His | 3.9 |
| L-Thr-NH₂ | L-Gln | L-Thr-L-Gln | 0.3 |

(Hydrochloride salts were used for all of the carboxy components.)

Example 16

Substrate Specificity of Enzyme (7)

Peptide production by using various L-alanine methyl esters as the carboxy component and C-protected L-amino acids as the amine component was examined. 2 μl of the same enzyme fraction as used in Example 5 was added to 100 μl of 100 mM borate buffer (pH 9.0) containing 100 mM L-alanine methyl ester hydrochlorides (Ala-OMe.HCl) shown in Table 10, 150 mM L-amino acid amides shown in Table 10 and 10 mM EDTA, and allowed to react at 25° C. for 3 hours. The amounts of each of the peptides formed in this reaction are shown in Table 10.

TABLE 10

| Carboxy component | Amine component | Formed peptide (mM) | |
|---|---|---|---|
| L-Ala-OMe | Gly-NH₂ | L-Ala-Gly-NH₂ | 7.4 |
| | L-Ala-NH₂ | L-Ala-L-Ala-NH₂ | 8.3 |
| | L-Phe-NH₂ | L-Ala-L-Phe-NH₂ | 12.2 |

Example 17

Substrate Specificity of Enzyme (8)

Peptide production by using various amino acid methyl esters as the carboxy component and methylamine as the amine component was examined. 2 μl of the same enzyme fraction as used in Example 5 was added to 100 μl of 100 mM borate buffer (pH 9.0) containing 100 mM amino acid methyl ester hydrochlorides (AA-OMe.HCl) shown in Table 11, 150 mM methylamine shown in Table 11 and 10 mM EDTA, and allowed to react at 25° C. for 3 hours. The amounts of each of the peptides formed in this reaction are shown in Table 11.

TABLE 11

| Carboxy component | Amine component | Formed peptide (mM) | |
|---|---|---|---|
| Gly-OMe | Methylamine | Gly-methylamine | 1.1 |
| L-Thr-OMe | | L-Thr-methylamine | 0.2 |
| L-Ala-OMe | | L-Ala-methylamine | 0.3 |

(Hydrochloride salts were used for all of the carboxy components.)

Example 18

Substrate Specificity of Enzyme (9)

Peptide production by using β-amino acid esters as the carboxy component or β-amino acids as the amine component was examined. 2 μl of the same enzyme fraction as used in Example 5 was added to 100 μl of 100 mM borate buffer (pH 9.0) containing 100 mM carboxy components shown in Table 12 150 mM amine components shown in Table 12 and 10 mM EDTA, and allowed to react at 25° C. for 3 hours. The amounts of each of the peptides formed in this reaction are shown in Table 12. (The "tr" indicates a trace amount.)

TABLE 12

| Carboxy component | Amine component | Formed peptide (mM) |
|---|---|---|
| Gly-OMe | β-Ala | Gly-β-Ala | 2.2 |
| Gly-OMe | β-Phe | Gly-β-Phe | 0.4 |
| L-Ala-OMe | β-Ala | Ala-β-Ala | 7.7 |
| L-Ala-OMe | β-Phe | Ala-β-Phe | 1.4 |
| L-Thr-OMe | β-Ala | Thr-β-Ala | 3.2 |
| L-Thr-OMe | β-Phe | Thr-β-Phe | 1.4 |
| β-Ala-OMe | L-α-Ala | β-Ala-L-α-Ala | tr |
| β-Ala-OMe | β-Ala | β-Ala-β-Ala | 0.2 |
| B-Ala-OMe | L-Gln | β-Ala-L-Gln | 0.6 |
| B-Ala-OMe | L-Ser | β-Ala-L-Ser | 3.2 |

Example 19

Substrate Specificity of Enzyme (10)

Oligopeptide production by using L-amino acid ester as the carboxy component and peptide as the amine component was examined. 2 μl of the same enzyme fraction as used in Example 5 was added to 100 μl of 100 mM borate buffer (pH 9.0) containing 100 mM carboxy components shown in Table 13, 150 mM amine components shown in Table 13 and 10 mM EDTA, and allowed to react at 25° C. for 3 hours. The amounts of each of the peptides formed in this reaction are shown in Table 13. As a result, it was clearly demonstrated that the present enzyme can form not only dipeptide, but also long-chain peptides by using a peptide as the amine component.

As has been indicated in the aforementioned Examples 9 to 19, the present enzyme obtained from *Empedobacter brevis* FERM BP-18545 was determined to have extremely broad substrate specificity.

TABLE 13

| Carboxy component | Amine component | Produced peptide (mM) | |
|---|---|---|---|
| L-Ala-OMe | L-Ala | L-Ala-L-Ala | 28.7 |
| | L-Ala-L-Ala | L-Ala-L-Ala-L-Ala | 57.5 |
| | L-Ala-L-Ala-L-Ala | L-Ala-L-Ala-L-Ala-L-Ala | 44.5 |
| | L-Ala-L-Ala-L-Ala-L-Ala | L-Ala-L-Ala-L-Ala-L-Ala-L-Ala | 34.8 |
| | L-Ala-L-Ala-L-Ala-L-Ala-L-Ala | L-Ala-L-Ala-L-Ala-L-Ala-L-Ala-L-Ala | 1.4* |
| | L-Ala-L-Gln | L-Ala-L-Ala-L-Gln | 15.2 |
| | Gly-L-Ala | L-Ala-Gly-L-Ala | 25.9 |
| | Gly-Gly | L-Ala-Gly-Gly | 41.7 |
| | L-His-L-Ala | L-Ala-L-His-L-Ala | 55.9 |
| | L-Leu-L-Ala | L-Ala-L-Leu-L-Ala | 48.3 |
| | L-Phe-L-Ala | L-Ala-L-Phe-L-Ala | 49.7 |
| | L-Phe-Gly | L-Ala-L-Phe-Gly | 43.7 |
| Gly-OMe | L-Ala-L-Tyr | Gly-L-Ala-L-Tyr | 1.7 |
| | Gly-L-Gln | Gly-Gly-L-Gln | 7.2 |
| | Gly-L-Tyr-L-Ala | Gly-Gly-L-Tyr-L-Ala | 44.2 |
| L-Thr-OMe | Gly-Gly | L-Thr-Gly-Gly | 83.0 |

(*Since the solubility of L-Ala-L-Ala-L-Ala-L-Ala-L-Ala-L-Ala was low, the carboxy component was used at a concentration of 10 mM and the amine component was used at 15 mM in this reaction system. The other conditions were the same as those explained in the example.)

Example 20

Comparison of Ability to Catalyze Peptide Formation with Known Enzymes

The peptide-forming ability of the present enzyme was compared with that of known enzymes. Carboxypeptidase Y described in EP 278787A1 and the thiol endopeptidases (ficin, papain, bromelain, and chymopapain) described in EP 359399B1 were used for the known enzymes, and they were used in the form of purified enzymes manufactured by Sigma. Homogeneously purified samples were used as the enzyme in Example 3. The enzymes were added to the reaction system. The amount of the enzyme was shown in Table 14 in terms of the amount of protein. The reaction was carried out by adding the enzyme to 100 μl of borate buffer (pH 9.0) containing 100 mM L-alanine methyl ester and 200 mM L-glutamine and allowing the resultant to react at 25° C. Note that the carboxypeptidase used was one dissolved in 10 mM acetate buffer (pH 5.0) containing 1 mM EDTA, while each thiol endopeptidase used was one dissolved in 10 mM acetate buffer (pH 5.0) containing 2 mM EDTA, 0.1 M KCl, and 5 mM dithiothreitol. The ratios of the production rates of L-alanyl-L-glutamine by these enzymes are shown in Table 14.

As a result, the production of an extremely small amount of L-alanyl-L-glutamine was observed even in the absence of enzymes, while a slight increase in the production rate was observed in the carboxypeptidase- or thiol endopeptidase-added lot as compared with the enzyme-non-added lot. In contrast, an overwhelmingly higher rate of production of L-alanyl-L-glutamine was observed in the present enzyme-added lot, and that rate of production was about 5,000 to 100,000 folds higher than those of carboxypeptidase Y and thiol endopeptidases. As has been described above, the present enzyme was verified to have an extremely high peptide production rate in contrast to any known enzyme. Furthermore, the present enzyme is a dimer having a molecular weight of about 75,000. In contrast, the carboxypeptidase Y has been reported to have a molecular weight of about 61,000, while the thiol endopeptidases have been reported to have a molecular weight of about 23,000 to 36,000. Thus, the present enzyme is much higher than the carboxypeptidase Y and the thiol endopeptidase when expressed in an L-alanyl-L-glutamine production rate per molecular weight as compared to when expressed in L-alanyl-L-glutamine production rate per unit weight as indicated in the examples.

TABLE 14

| Enzyme | Amount of enzyme added (protein mg/ml) | L-Ala-L-Gln production rate(mM/min) | Ratio of L-Ala-L-Gln production rate per enzyme unit weight |
|---|---|---|---|
| No enzyme | 0 | 0.0006 | |
| Carboxypeptidase Y | 0.61 | 0.0257 | 0.0191 |
| Ficin | 2.60 | 0.0096 | 0.0017 |
| Papain | 2.30 | 0.0106 | 0.0021 |
| Bromelain | 2.80 | 0.0062 | 0.0010 |
| Chymopapain | 3.60 | 0.0100 | 0.0013 |
| Enzyme of present invention | 0.02 | 4.4000 | 100.0 |

Example 21

Isolation of Peptide-Forming Enzyme Gene Derived from *Empedobacter brevis*

Hereinafter, isolation of a peptide-forming enzyme gene will be explained. The microbe used was *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). For isolating the gene, *Escherichia coli* JM-109 was used as a host and pUC118 was used as a vector.

(1) Construction of PCR Primer Based on Determined Internal Amino Acid Sequence

A Mixed primer having the base sequences indicated in SEQ ID NO: 3 and SEQ ID NO: 4, respectively, was constructed based on the amino acid sequences (SEQ ID NOs: 1 and 2) determined by the Edman's decomposition method detecting a digestion product of a peptide-forming enzyme derived from the *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) digested by a lysyl endopeptidase.

(2) Preparation of Microbial Cells

*Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultivated at 30° C. for 24 hours on a CM2G agar medium (containing 50 g/l glucose, 10 g/l yeast extract, 10 g/l peptone, 5 g/l sodium chloride, and 20 g/l agar, pH 7.0). One loopful cells of the resulting microbial cells was inoculated into a 500 ml Sakaguchi flask containing 50 ml of a CM2G liquid medium (the aforementioned medium excluding agar) followed by shaking cultivation at 30° C.

(3) Preparation of Chromosomal DNA from Microbial Cells

First, 50 ml of culture broth was centrifuged (12,000 rpm, 4° C., 15 minutes) to collect the microbial cells. Then, a chromosomal DNA was obtained from the microbial cells using the QIAGEN Genomic-Tip System (Qiagen) based on the procedure described in the manual therefor.

(4) Preparation of DNA Fragment Containing a Portion of Gene for Peptide-forming Enzyme by PCR A DNA fragment containing a portion of gene for the peptide-forming enzyme derived from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out by using the primers having the base sequences of SEQ ID NOs: 3 and 4 to a chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002).

The PCR reaction was carried out for 30 cycles under the following conditions using Takara PCR Thermal Cycler PERSONAL (manufactured by Takara Shuzo).

94° C. 30 seconds

52° C. 1 minute

72° C. 1 minute

After the reaction, 3 µl of the reaction mixture was applied to 0.8% agarose electrophoresis. As a result, it was verified that a DNA fragment of about 1.5 kilobases (kb) was amplified.

(5) Cloning of Gene for Peptide-Forming Enzyme from Gene Library

In order to obtain the gene for peptide-forming enzyme in full-length, southern hybridization was carried out by using the DNA fragment amplified in the PCR procedure as a probe. The procedure for southern hybridization is explained in Molecular Cloning, 2nd edition, Cold Spring Harbor Press (1989).

The approximately 1.5 kb DNA fragment amplified by the PCR procedure was separated by 0.8% agarose electrophoresis. The target band was then cut out and purified. The DNA fragment was labeled with digoxinigen as probe by using DIG High Prime (manufactured by Boehringer-Mannheim) based on the procedure described in the manual therefor.

After completely digesting the chromosomal DNA of *Empedobacter brevis* obtained in the step (3) of the present Example 21 by reacting at 37° C. for 16 hours with restriction enzyme HindIII, the resultant was electrophoresed on 0.8% agarose gel. The electrophoresed chromosomal DNA was blotted onto a positively charged Nylon membrane filter (manufactured by Roche Diagnostics) from the agarose gel after the electrophoresis, followed by treatments of alkali denaturation, neutralization and immobilization. Hybridization was carried out by using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed for 20 minutes at room temperature with 2×SSC containing 0.1% SDS. Moreover, the filter was additionally washed twice at 65° C. for 15 minutes with 1×SSC.

Detection of bands that hybridized with the probe was carried out by using the DIG Nucleotide Detection Kit (manufactured by Boehringer-Mannheim) based on the procedure described in the manual therefor. As a result, an about 4 kb band was able to be detected that hybridized with the probe.

Then, 5 μg of the chromosomal DNA prepared in the step (3) of the present Example 21 was completely digested with HindIII. An about 4 kb DNA was separated by 0.8% agarose gel electrophoresis, followed by purification of the DNA using the Gene Clean II Kit (manufactured by Funakoshi) and dissolving the DNA in 10 μl of TE. 4 μl of this product was then mixed with pUC118 HindIII/BAP (manufactured by Takara Shuzo) and a ligation reaction was carried out by using the DNA Ligation Kit Ver. 2 (manufactured by Takara Shuzo). 5 μl of the ligation reaction mixture and 100 μl of competent cells of *Escherichia coli* JM109 (manufactured by Toyobo) were mixed to transform the *Escherichia coli*. This was then applied to a suitable solid medium to construct a chromosomal DNA library.

To obtain the full-length gene for peptide-forming enzyme, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred on a Nylon membrane filter (Nylon Membrane for Colony and Plaque Hybridization (manufactured by Roche Diagnostics) followed by treatments of alkali denaturation, neutralization and immobilization. Hybridization was carried out by using EASY HYB (manufactured by Boehringer-Mannheim). After pre-hybridizing the filter at 37° C. for 1 hour, the aforementioned probe labeled with digoxinigen was added, followed by hybridization at 50° C. for 16 hours. Subsequently, the filter was washed for 20 minutes at room temperature with 2×SSC containing 0.1% SDS. In addition, the filter was additionally washed twice at 65° C. for 15 minutes with 1×SSC.

Detection of colonies hybridizing with the labeled probe was carried out by using the DIG Nucleotide Detection Kit (manufactured by Boehringer-Mannheim) based on the explanation described in the manual therefor. As a result, two strains of colonies were verified to hybridize with the labeled probe.

(6) Base Sequence of Gene for Peptide-Forming Enzyme Derived from *Empedobacter brevis*

Plasmids possessed by *Escherichia coli* JM109 were prepared from the aforementioned two strains of microbial cells that were verified to hybridize with the labeled probe by using the Wizard Plus Minipreps DNA Purification System (manufactured by Promega) and the base sequence of a portion where hybridization with the probe occurred and nearby was determined. The sequencing reaction was carried out by using the CEQ DTCS-Quick Start Kit (manufactured by Beckman-Coulter) based on the procedure described in the manual therefor. In addition, electrophoresis was carried out by using the CEQ 2000-XL (manufactured by Beckman-Coulter).

As a result, it was verified that an open reading frame that encodes a protein containing the internal amino acid sequences of the peptide-forming enzyme (SEQ ID NOs: 1 and 2) did exist, and that the open reading frame was a gene encoding the peptide-forming enzyme. The base sequence of the full-length gene for peptide-forming enzyme along with the corresponding amino acid sequences is shown in SEQ ID NO: 5. As a result of analysis on the homology of the resulting open reading frame with the BLASTP program, homology was discovered with two enzymes; it showed a homology of 34% as amino acid sequence with the a-amino acid ester hydrolase of *Acetobacter pasteurianus* (see Appl. Environ. Microbiol., 68(1), 211-218 (2002), and a homology of 26% as amino acid sequence with the glutaryl-7ACA acylase of *Brevibacillus laterosporum* (see J. Bacteriol., 173(24), 7848-7855 (1991).

Example 22

Expression of Gene for Peptide-Forming Enzyme Derived from *Empedobacter brevis* in *Escherichia coli*

The promoter region of the trp operon on the chromosomal DNA of *Escherichia coli* W3110 was amplified by PCR using the oligonucleotides indicated in SEQ ID NOs: 7 and 8 as primers, and the resulting DNA fragments were ligated to a pGEM-Teasy vector (manufactured by Promega). *Escherichia coli* JM109 was then transformed with this ligation solution, and those strains having the target plasmid in which the direction of the inserted trp promoter is opposite to the orientation of the lac promoter were selected from ampicillin-resistant strains. Next, a DNA fragment containing the trp promoter obtained by treating this plasmid with EcoO109I/EcoRI was ligated to an EcoO109I/EcoRI treatment product of pUC19 (manufactured by Takara). *Escherichia coli*JM109 was then transformed with this ligation solution and those strains having the target plasmid were selected from ampicillin-resistant strains. Next, a DNA fragment obtained by treating this plasmid with HindIII/PvuII was ligated to a DNA fragment containing an rrnB terminator obtained by treating pKK223-3 (manufactured by Amersham Pharmacia) with HindIII/HincII. *Escherichia coli* JM109 was then transformed with this ligation solution, strains having the target plasmid were selected from ampicillin-resistant strains, and the plasmid was designated as pTrpT.

The target gene was amplified by PCR using the chromosomal DNA of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) as a template and the oligonucleotides indicated in SEQ ID NOs: 9 and 10 as primers. This DNA fragment was then treated with NdeI/PstI, and the resulting DNA fragment was ligated with the NdeI/PstI treatment product of pTrpT. *Escherichia coli* JM109 was then transformed with this ligation solution, those strains having the target plasmid were selected from ampicillin-resistant strains, and this plasmid was designated as pTrpT_Gtg2.

*Escherichia coli* JM109 having pTrpT_Gtg2 was seed cultured at 30° C. for 24 hours in LB medium containing 100 mg/l of ampicillin. 1 ml of the resulting culture broth was transferred in a 500 ml Sakaguchi flask containing 50 ml of a medium (D-glucose 2 g/l, yeast extract 10 g/l, casamino acid 10 g/l, ammonium sulfate 5 g/l, potassium dihydrogen phosphate 3 g/l, dipotassium hydrogen phosphate 1 g/l, magnesium sulfate heptahydrate 0.5 g/l, and ampicillin 100 mg/l), followed by cultivation at 25° C. for 24 hours. The culture broth had an L-alanyl-L-glutamine production activity of 0.44 Upper ml of culture broth and it was verified that the cloned gene was expressed by *Escherichia coli*. Furthermore, no activity was detected for a transformant in which only pTrpT had been introduced as a control.

(Prediction of Signal Sequence)

When the amino acid sequence of SEQ ID NO: 6 described in the Sequence Listing was analyzed with the Signal P v 1.1 program (see Protein Engineering, Vol. 12, No. 1, pp. 3-9, 1999), it was predicted that numbers 1 to 22 in amino acid sequences was operated as a signal to secrete into the periplasm, while the mature protein was estimated to be downstream of amino acid number 23.

(Verification of Secretion)

*Escherichia coli* JM109, having pTrpT_Gtg2, was seed cultured at 30° C. for 24 hours in LB medium containing 100 mg/l of ampicillin. 1 ml of the resulting culture broth was transferred into a 500 ml Sakaguchi flask containing 50 ml of medium (glucose 2 g/l, yeast extract 10 g/l, casamino acid 10 g/l, ammonium sulfate 5 g/l, potassium dihydrogen phosphate 3 g/l, dipotassium hydrogen phosphate 1 g/l, magnesium sulfate heptahydrate 0.5 g/l, and ampicillin 100 mg/l), followed by final cultivation at 25° C. for 24 hours to obtain cultured microbial cells.

The cultured microbial cells were fractionated into a periplasm fraction and a cytoplasm fraction by an osmotic pressure shock method using a 20 grams/deciliter (g/dl) sucrose solution. The microbial cells immersed in the 20 g/dl sucrose solution were immersed in a 5 mM aqueous $MgSO_4$ solution. The centrifuged supernatant was named a periplasm fraction (Pe). In addition, the centrifuged sediment was re-suspended and subjected to ultrasonic disrupting. The resultant was named a cytoplasm fraction (Cy). The activity of glucose 6-phosphate dehydrogenase, which is known to be present in the cytoplasm, was used as an indicator to verify that the cytoplasm had been separated. This measurement was carried out by adding a suitable amount of enzyme to a reaction mixture at 30° C. containing 1 mM glucose 6-phosphate, 0.4 mM NADP, 10 mM $MgSO_4$, and 50 mM Tris-Cl (pH 8), followed by measurement of absorbance at 340 nm to measure production of NADPH.

Figure 4:
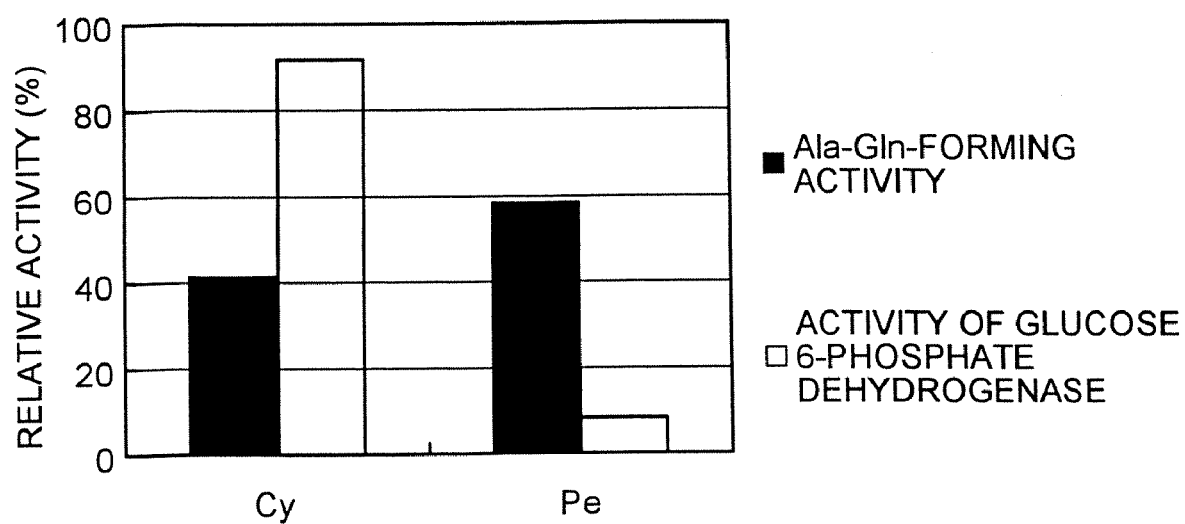
FIG. 4 shows amounts of an enzyme existing in a cytoplasm fraction (Cy) and a periplasm fraction (Pe).

The amounts of enzymes in the periplasm fraction and the cytoplasm fraction when the activity of a separately prepared cell-free extract was assigned a value of 100% are shown in FIG. 4. That glucose 6-phosphate dehydrogenase activity did not contain in the periplasm fraction indicates that the periplasm fraction did not mix with the cytoplasm fraction. About 60% of the Ala-Gln production activity was recovered in the periplasm fraction, and it was verified that the Ala-Gln-forming enzyme was secreted into the periplasm as predicted from the amino acid sequence using the Signal P v 1.1 program.

Example 23

Substrate Specificity of Enzyme (11)

Using an enzyme fraction having an Ala-Gln-producing activity prepared from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002), the substrate specificity thereof was further examined. A 100 µl reaction mixture consisting of 100 mM borate buffer (pH 9.0) containing various carboxy components and amine components at the final concentrations shown in Table 15, enzyme (0.1 units added to the reaction mixture), and 10 mM EDTA were allowed to react at 25° C. for the reaction times shown in Table 15. The production amounts of each of the peptides produced in this reaction are shown in Table 15. (The "+" mark indicates that peptides production was confirmed but were unable to be quantified due to the absence of a standard preparation, while "tr" indicates a trace amount.)

TABLE 15

| Carboxy component (mM) | | Amine component (mM) | | Produced peptide (mM) | | Reaction time (hr) |
|---|---|---|---|---|---|---|
| H-Ala-OMe | 50 mM | H-p-F-Phe-OH | 50 mM | H-Ala-p-F-Phe-OH | 21.9 mM | 3 |
| H-Ala-OMe | 40 mM | H-Cl-F-Phe-OH | 40 mM | H-Ala-Cl-F-Phe-OH | 20.8 mM | 3 |
| H-Ala-OMe | 40 mM | H-p-$NO_2$-Phe-OH | 40 mM | H-Ala-p-$NO_2$-Phe-OH | 27.5 mM | 3 |
| H-Ala-OMe | 100 mM | H-t-Leu-OH | 150 mM | H-Ala-t-Leu-OH | 0.4 mM | 3 |
| H-Ala-OMe | 20 mM | H-2-Nal-OH | 20 mM | H-Ala-2-Nal-OH | + | 3 |
| H-p-F-Phe-OMe | 100 mM | H-Gln-OH | 150 mM | H-p-F-Phe-H-Gln-OH | tr | 3 |
| H-Cl-F-Phe-OMe | 25 mM | H-Gln-OH | 50 mM | H-Cl-F-Phe-H-Gln-OH | tr | 3 |
| H-p-$NO_2$-Phe-OMe | 40 mM | H-Gln-OH | 40 mM | H-p-$NO_2$-Phe-H-Gln-OH | 1.1 mM | 3 |
| H-t-Leu-OMe | 100 mM | H-Gln-OH | 150 mM | H-t-Leu-H-Gln-OH | tr | 3 |
| H-2-Nal-OMe | 40 mM | H-Gln-OH | 40 mM | H-2-Nal-H-Gln-OH | tr | 3 |
| H-Aib-OMe | 100 mM | H-Gln-OH | 150 mM | H-Aib-H-Gln-OH | 18.8 mM | 3 |
| H—N-Me-Ala-OMe | 100 mM | H-Gln-OH | 150 mM | H—N-Me-Ala-H-Gln-OH | 0.5 mM | 3 |
| H-Aib-OMe | 100 mM | H-Phe-OH | 150 mM | H-Aib-Phe-OH | 17.2 mM | 3 |
| H-CHA-OMe | 40 mM | H-Phe-OH | 40 mM | H-CHA-Phe-OH | + | 3 |
| H—N-Me-Ala-OMe | 100 mM | H-Phe-OH | 150 mM | H—N-Me-Ala-Phe-OH | tr | 3 |
| H-Ala-OMe | 100 mM | H-Ser(tBu)-OH | 150 mM | H-Ala-Ser(tBu)-OH | 48.8 mM | 2 |
| H-Ser(tBu)-OMe | 100 mM | H-Gln-OH | 150 mM | H-Ser(tBu)-Gln-OH | tr | 2 |
| H-Ala-OMe | 100 mM | H-Asp(OtBu)-OH | 150 mM | H-Ala-Asp(OtBu)-OH | 62.6 mM | 2 |
| H-Asp(OtBu)-OMe | 100 mM | H-Gln-OH | 150 mM | H-Asp(OtBu)-Gln-OH | 0.9 mM | 2 |
| H-Ala-OMe | 100 mM | H-Lys(Boc)-OH | 150 mM | H-Ala-Lys(Boc)-OH | 51.0 mM | 2 |
| H-Lys(Boc)-OMe | 100 mM | H-Gln-OH | 150 mM | H-Lys(Boc)-Gln-OH | + | 2 |

Explanation of abbreviations;
H-Ala-OMe: L-Alanine methyl ester hydrochloride
H-p-F-Phe-OMe: p-Fluoro-L-phenylalanine methyl ester hydrochloride
H-Cl-F-Phe-OMe: p-Chloro-L-phenylalanine methyl ester hydrochloride
H-p-$NO_2$-Phe-OMe: p-Nitro-L-phenylalanine methyl ester hydrochloride
H-t-Leu-OMe: tert-L-Leucine methyl ester hydrochloride
H-2-Nal-OMe: 3-(2-Naphthyl)-L-alanine methyl ester hydrochloride
H-Aib-OMe: α-Aminoisobutyric acid methyl ester hydrochloride
H—N-Me-Ala-OMe: N-Methyl-L-alanine methyl ester hydrochloride
H-CHA-OMe: β-Cyclohexyl-L-alanine methyl ester hydrochloride
H-Ser(tBu)-OMe: O-tert-Butyl-L-serine methyl ester hydrochloride
H-Asp(OtBu)-OMe: L-Aspartic acid β-tert-butyl ester α-methyl ester hydrochloride
H-Lys(Boc)-OMe: N-ε-tert-Butoxycarbonyl-L-lysine methyl ester hydrochloride
H-p-F-Phe-OH: p-Fluoro-L-phenylalanine
H-Cl-F-Phe-OH: p-Chloro-L-phenylalanine
H-p-$NO_2$-Phe-OH: p-Nitro-L-phenylalanine
H-t-Leu-OH: tert-L-Leucine H-2-Nal-OH: 3-(2-Naphthyl)-L-alanine
H-Gln-OH: L-Glutamine
H-Phe-OH: L-Phenylalanine
H-Ser(tBu)-OH: O-tert-Butyl-L-serine
H-Asp(OtBu)-OH: L-Aspartic acid β-tert-butyl ester
H-Lys(Boc)-OH: N-ε-tert-Butoxycarbonyl-L-lysine

Example 24

Substrate Specificity of Enzyme (12)

Using the same enzyme fraction as that in Example 23, substrate specificity with respect to oligopeptide production was examined. 100 μl of a reaction mixture consisting of a 10 mM EDTA-containing 100 mM borate buffer (pH 9.0) containing various carboxy components and amine components at the final concentrations shown in Table 16, and an enzyme (unit numbers added to the reaction mixture are described in Table 18) were allowed to react at 25° C. for 3 hours. The amounts of each kind of the oligopeptides produced in this reaction are shown in Table 18 (the "+" mark indicates that peptides production was confirmed but were unable to be quantified due to the absence of standard preparations, while "tr" indicates a trace amount). Furthermore, hydrochlorides were used for all the carboxy components.

TABLE 16

| Carboxy component | Amine component | Amount of enzyme | Produced peptide (mM) | |
|---|---|---|---|---|
| Gly-OMe | L-Phe-L-Met | 1.0 | Gly-Phe-Met | 13.3 |
| L-Ala-OMe | L-Phe-L-Met | 0.2 | L-Ala-L-Phe-L-Met | + |
| L-Tyr-OMe | Gly-Gly-L-Phe-L-Met | 1.0 | L-Tyr-Gly-Gly-L-Phe-L-Met | 2.7 |
| L-Ala-OMe | Gly-Gly-L-Phe-L-Met | 0.2 | L-Ala-Gly-Gly-L-Phe-L-Met | + |
| Gly-OMe | Gly-L-Phe | 0.1 | Gly-L-Phe | 17.3 |
| L-Ala-OMe | Gly-L-Phe | 0.1 | L-Ala-Gly-L-Phe | + |
| D-Ala-OMe | Gly-L-Phe | 0.1 | D-Ala-Gly-L-Phe | Tr |

Example 25

Production of L-Alanyl-L-Glutamine Using Microbial Cells of *Sphingobacterium* sp.

A 50 ml medium (pH 7.0) containing 5 g glucose, 5 g ammonium sulfate, 1 g monopotassium phosphate, 3 g dipotassium phosphate, 0.5 g magnesium sulfate, 10 g yeast extract and 10 g peptone in 1 L was transferred to a 500 mL Sakaguchi flask and sterilized at 115° C. for 15 minutes for culturing *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). This was then inoculated with one loopful cells of *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) cultivated at 30° C. for 24 hours on a slant agar medium (pH 7.0) containing 5 g glucose, 10 g yeast extract, 10 g peptone and 5 g NaCl and 20 g/L agar in 1 L, followed by shaking cultivation at 30° C. for 20 hours and 120 strokes/minute. 1 ml of this culture broth was then added to the aforementioned medium (50 ml/500 mL Sakaguchi flask) and cultivated at 30° C. for 18 hours. After the cultivation, the microbial cells were separated from the culture broth by centrifugation and suspended in 0.1 M borate buffer (pH 9.0) containing 10 mM EDTA to 100 g/L cells as wet basis. 0.1 mL of 100 mM borate buffer (pH 9.0) containing 10 mM EDTA, 200 mM L-alanyl methyl ester hydrochloride and 400 mM L-glutamine was then added to 0.1 mL of this microbial cell suspension to bring a final volume 0.2 mL, was allowed to react at 25° C. for 120 minutes. The amount of L-alanyl-L-glutamine formed was 62 mM.

Example 26

Purification of Enzyme from *Sphingobacterium* sp.

The following procedure after centrifugal separation was carried out either on ice or at 4° C. *Sphingobacterium* sp. FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultivated in the same manner as Example 25, and the microbial cells were collected by centrifugal separation (10,000 rpm, 15 minutes). After washing 2 g of microbial cells with 20 mM Tris-HCl buffer (pH 7.6), they were suspended in 8 ml of the same buffer and subjected to ultrasonic disrupting treatment for 45 minutes at 195 W. This ultrasonically disrupted solution was then centrifuged (10,000 rpm, 30 minutes) to remove the cell debris and obtain an ultrasonically disrupted supernatant. This supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant solution. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0) followed by removal of the insoluble fraction by centrifugal separation (10,000 rpm, 30 minutes) to obtain a dialyzed fraction in the form of the supernatant solution. This supernatant was then applied to an SP-Sepharose HP column (manufactured by Amersham) pre-equilibrated with 20 mM acetate buffer (pH 5.0) to obtain the active fraction in which enzyme was eluted with a linear concentration gradient of the same buffer containing 0 to 1 M NaCl.

Example 27

Production of L-Alanyl-L-Glutamine Using Enzyme Fraction

10 µl of the SP-Sepharose HP fraction (about 27 U/ml) purified in Example 26 was added to 90 µl of 111 mM borate buffer (pH 9.0) containing 111 mM L-alanine methyl ester hydrochloride, 222 mM L-glutamine and 11 mM EDTA, and allowed to react at 25° C. for 120 minutes. As a result, 73 mM of L-alanyl-L-glutamine was formed in the enzyme-added lot. On the other hand, there was scarcely any production of L-Ala-L-Glu observed in the enzyme-non-added lot, and the production amount was only about 0.07 mM after reaction for 120 minutes.

Example 28

Substrate Specificity of Enzyme (13)

Substrate specificity of the enzyme from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was examined. 100 µl of 100 mM borate buffer (pH 9.0) containing the various carboxy components at a final concentration of 100 mM and the various amine components at a final concentration of 150 mM shown in Tables 17-1 to 17-4, the SP-Sepharose HP fraction enzyme purified in Example 26 (addition of 0.33 units in the reaction mixture) and EDTA at a final concentration of 10 mM were allowed to react at 25° C. for 1.5 hours. The amounts of each of the peptides formed in this reaction are shown in Table 17. (The "+" mark indicates that peptides production was confirmed but were unable to be quantified due to the absence of a standard, while "tr" indicates a trace amount.) Furthermore, Tween-80 was added to the reaction mixture to a final concentration of 0.1% in the case of using L-Tyr-OMe. In addition, hydrochlorides were used for all carboxy components.

TABLE 17

| Carboxy component | Amine component | Produced peptide | (mM) |
|---|---|---|---|
| L-Ala-OMe | Gly | L-Ala-Gly | 11.1 |
|  | L-Ala | L-Ala-L-Ala | 13.1 |

TABLE 17-continued

| Carboxy component | Amine component | Produced peptide | (mM) |
|---|---|---|---|
|  | L-Val | L-Ala-L-Val | 10.9 |
|  | L-Leu | L-Ala-L-Leu | 33.0 |
|  | L-Ile | L-Ala-L-Ile | 24.7 |
|  | L-Met | L-Ala-L-Met | 86.9 |
|  | L-Pro | L-Ala-L-Pro | 1.5 |
|  | L-Phe | L-Ala-L-Phe | 69.5 |
|  | L-Trp | L-Ala-L-Trp | 46.0 |
|  | L-Thr | L-Ala-L-Thr | 47.3 |
|  | L-Asn | L-Ala-L-Asn | 52.3 |
|  | L-Tyr | L-Ala-L-Tyr | 11.1 |
|  | L-CySH | L-Ala-L-CySH | + |
|  | L-Lys | L-Ala-L-Lys | 71.2 |
|  | L-Arg | L-Ala-L-Arg | 72.2 |
|  | L-His | L-Ala-L-His | 73.6 |
|  | L-Asp | L-Ala-L-Asp | 2.3 |
|  | L-Glu | L-Ala-L-Glu | 39.1 |
|  | L-Ser | L-Ala-L-Ser | 43.8 |
|  | D-Ser | L-Ala-D-Ser | 3.3 |
| D-Ala-OMe | L-Ser | D-Ala-L-Ser | 24.1 |
|  | D-Ser | D-Ala-D-Ser | 5.5 |
| L-Thr-OMe | L-Gln | L-Thr-L-Gln | 36.1 |
| Gly-OMe |  | Gly-L-Gln | 61.1 |
| L-Ser-OMe |  | L-Ser-L-Gln | 12.9 |
| L-Val-OMe |  | L-Val-L-Gln | 8.2 |
| L-Met-OMe |  | L-Met-L-Gln | 32.6 |
| L-Ile-OMe |  | L-Ile-L-Gln | 6.4 |
| L-Arg-OMe |  | L-Arg-L-Gln | 17.2 |
| L-Tyr-OMe |  | L-Tyr-L-Gln | 0.6 |
| L-Pro-OMe |  | L-Pro-L-Gln | 1.8 |
| L-Phe-OMe |  | L-Phe-L-Gln | 0.8 |
| L-Gln-OMe |  | L-Gln-L-Gln | 0.1 |
| Asp-α-OMe |  | α-L-Asp-L-Gln | 0.05 |
| L-Thr-OMe | Gly | L-Thr-Gly | 0.4 |
|  | L-Ala | L-Thr-L-Ala | 5.8 |
|  | L-Val | L-Thr-L-Val | 1.3 |
|  | L-Leu | L-Thr-L-Leu | 15.3 |
|  | L-Met | L-Thr-L-Met | 28.9 |
| Gly-OMe | L-Arg | Gly-L-Arg | 17.9 |
|  | L-Phe | Gly-L-Phe | 20.0 |
|  | L-His | Gly-L-His | 36.2 |
|  | L-Lys | Gly-L-Lys | 48.2 |
|  | L-Ser | Gly-L-Ser | 53.8 |
| L-Ser-OMe | L-Ser | L-Ser-L-Ser | 9.9 |
|  | L-Met | L-Ser-L-Met | 7.6 |
|  | L-Phe | L-Ser-L-Phe | 4.3 |
| L-Val-OMe | L-Ser | L-Val-L-Ser | 31.9 |
|  | L-Met | L-Val-L-Met | 6.8 |
|  | L-Phe | L-Val-L-Phe | 1.0 |
| L-Met-OMe | L-Ser | L-Met-L-Ser | 25.3 |
|  | L-Met | L-Met-L-Met | 28.4 |
|  | L-Phe | L-Met-L-Phe | 8.9 |
| L-Ile-OMe | L-Ser | L-Ile-L-Ser | 17.3 |
|  | L-Met | L-Ile-L-Met | 5.1 |
|  | L-Phe | L-Ile-L-Phe | 1.5 |
| L-Arg-OMe | L-Ser | L-Arg-L-Ser | 2.2 |
|  | L-Met | L-Arg-L-Met | tr |
|  | L-Phe | L-Arg-L-Phe | tr |
| L-Ala-OMe | Gly amide | L-Ala-Gly amide | 15.1 |
|  | L-Ala amide | L-Ala-L-Ala amide | 9.2 |
|  | L-Phe amide | L-Ala-Phe amide | 27.1 |
| L-Ala-OMe | methylamine | L-Ala-methylamine | 0.6 |
| L-Thr-OMe |  | L-Thr-methylamine | 0.3 |
| Gly-OMe |  | Gly-methylamine | 1.0 |
| L-Ala amide | L-Gln | L-Ala-L-Gln | 0.3 |
|  | L-Met | L-Ala-L-Met | tr |
|  | L-His | L-Ala-L-His | tr |

Example 29

Substrate Specificity of Enzyme (14)

Substrate specificity with respect to oligopeptide production was examined for enzyme derived from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). 100 µl of 100 mM borate buffer (pH 9.0) containing the various carboxy components at a final concentration of 100 mM and the various amine components at a final concentration of 150 mM shown in Table 18, the SP-Sepharose HP fraction enzyme purified in Example 26 (addition of 0.33 units in the reaction mixture) and EDTA at a final concentration of 10 mM were allowed to react for 1.5 hours at 25° C. The amounts of each oligopeptide formed in this reaction are shown in Table 18. Note that hydrochlorides were used for all carboxy components.

TABLE 18

| Carboxy component | Amine component | Produced peptide (mM) | |
|---|---|---|---|
| L-Ala-OMe | L-Ala | L-Ala-L-Ala | 25.6 |
| | L-Ala-L-Ala | L-Ala-L-Ala-L-Ala | 41.1 |
| | L-Ala-L-Ala-L-Ala | L-Ala-L-Ala-L-Ala-L-Ala | 30.1 |
| | L-Ala-L-Ala-L-Ala-L-Ala | L-Ala-L-Ala-L-Ala-L-Ala-L-Ala | 22.8 |
| | Gly-Gly | L-Ala-Gly-Gly | 33.7 |
| | Gly-Ala | L-Ala-Gly-L-Ala | 35.1 |
| | L-His-L-Ala | L-Ala-L-His-L-Ala | 58.0 |
| | L-Phe-Gly | L-Ala-L-Phe-Gly | 34.0 |
| | L-Leu-L-Ala | L-Ala-L-Leu-L-Ala | 40.7 |
| | L-Phe-L-Ala | L-Ala-L-Phe-L-Ala | 24.8 |
| L-Thr-OMe | Gly-Gly | L-Thr-Gly-Gly | 8.4 |
| Gly-OMe | L-Ala-L-Tyr | Gly-L-Ala-L-Tyr | 0.6 |

Example 30

Isolation of Gene for Peptide-Forming Enzyme Derived from *Sphingobacterium* sp.

Hereinafter, isolation of gene for a peptide-forming enzyme is described. The microbe used was *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). For the isolation of gene, *Escherichia coli* DH5α was used as a host, and pUC118 was used as a vector.

(1) Preparation of Microbial Cells

*Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultivated for 24 hours at 25° C. on CM2G agar medium (containing glucose 50 g/l, yeast extract 10 g/l, peptone 10 g/l, sodium chloride 5 g/l, and agar 20 g/l, pH 7.0). One loopful cells of the resulting microbial cells was inoculated into a 500 ml Sakaguchi flask containing 50 ml of CM2G liquid medium (the aforementioned medium excluding agar) followed by shaking cultivation at 25° C.

(2) Preparation of Chromosomal DNA from Microbial Cells 50 ml of culture broth was centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of gene for the peptide-forming enzyme derived from *Empedobacter brevis* FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out by using primers having the base sequences of SEQ ID NOs: 3 and 4 to the chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002).

The PCR reaction was carried out by using Takara PCR Thermal Cycler —PERSONAL (Takara Shuzo) for 30 cycles under the following conditions.

94° C. 30 seconds
52° C. 1 minute
72° C. 1 minute

After the reaction, 3 µl of reaction mixture was applied to 0.8% agarose electrophoresis. As a result, it was verified that a DNA fragment of about 1.5 kb was amplified.

(4) Cloning of Gene for Peptide-Forming Enzyme from Gene Library

In order to obtain the full-length gene for peptide-forming enzyme, southern hybridization was carried out by using the DNA fragment amplified in the aforementioned PCR procedure as a probe. The procedure of southern hybridization are explained in Molecular Cloning, 2nd edition, Cold Spring Harbor Press (1989).

The approximately 1.5 kb DNA fragment amplified by the aforementioned PCR procedure was separated by 0.8% agarose electrophoresis. The target band was then cut out and purified. This DNA fragment was labeled with digoxinigen as probe by using DIG High Prime (manufactured by Boehringer-Mannheim) based on the procedure described in the manual therefor.

After allowing the chromosomal DNA of *Sphingobacterium* sp. obtained in the step (2) of the present Example 30 to react with restriction enzyme SacI at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out by using EASY HYB (manufactured by Boehringer-Mannheim). After pre-hybridizing the filter at 37° C. for 1 hour, the digoxinigen-labeled probe prepared as described above was added and hybridization was carried out at 37° C. for 16 hours. Subsequently, the filter was washed twice at 60° C. with 2×SSC containing 0.1% SDS.

Detection of bands that hybridized with the probe was carried out by using the DIG Nucleotide Detection Kit (Boehringer-Mannheim) based on the procedure described in the manual therefor. As a result, an about 3 kb band was successfully detected that hybridized with the probe.

5 μg of the chromosomal DNA prepared in the step (2) of the present Example 30 was completely digested with SacI. About 3 kb of a DNA was separated by 0.8% agarose gel electrophoresis, the DNA was purified using the Gene Clean II Kit (manufactured by Funakoshi), and dissolved in 10 μl of TE. 4 μl of the resulting solution was mixed with pUC118 that had been allowed to react treated with SacI at 37° C. for 16 hours to completely digest it and then treated with alkaline phosphatase (*E. coli* C75) at 37° C. for 30 minutes and at 50° C. for 30 minutes and a ligation reaction was carried out by using the DNA Ligation Kit Ver. 2 (manufactured by Takara Shuzo). 5 μl of this ligation reaction mixture and 100 μl of competent cells of *Escherichia coli* DH5a (manufactured by Takara Shuzo) were mixed to transform the *Escherichia coli*. This was then applied to a suitable solid medium to produce a chromosomal DNA library.

To obtain full-length gene for peptide-forming enzyme, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred on a Nylon membrane filter (Nylon Membrane for Colony and Plaque Hybridization, manufactured by Roche Diagnostics), followed by treatments of alkali denaturation, neutralization, and immobilization. Hybridization was carried out by using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies hybridizing with the labeled probe was carried out by using the DIG Nucleotide Detection Kit (manufactured by Boehringer-Mannheim) based on the explanation described in the manual therefor. As a result, six strains of colonies were verified to have hybridized with the labeled probe.

(5) Base Sequence of Gene for Peptide-Forming Enzyme Derived from *Sphingobacterium* sp.

Plasmids possessed by *Escherichia coli* DH5a were prepared from the six strains of microbial cells that were verified to have hybridized with the labeled probe by using the Wizard Plus Minipreps DNA Purification System (manufactured by Promega) to determine the base sequence of a portion where hybridization with the probe occurred and nearby was determined. The sequencing reaction was carried out by using the CEQ DTCS-Quick Start Kit (manufactured by Beckman-Coulter) based on the procedure described in the manual therefor. In addition, electrophoresis was carried out by using the CEQ 2000-XL (manufactured by Beckman-Coulter).

As a result, it revealed that an open reading frame that encodes peptide-forming enzyme did exist. The full-length base sequence of gene for the peptide-forming enzyme derived from *Sphingobacterium* sp. along with the corresponding amino acid sequence is shown in SEQ ID NO: 11. Peptide-forming enzyme derived from *Sphingobacterium* sp. exhibited a homology of 63.5% at the amino acid sequence level to the peptide-forming enzyme derived from *Empedobacter brevis* (as determined using the BLASTP program).

Example 31

Expression of Gene for Peptide-forming Enzyme Derived from *Sphingobacterium* sp. in *Escherichia coli*

The target gene was amplified by PCR using the chromosomal DNA of *Sphingobacterium* sp. FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) as a template and the oligonucleotides shown in SEQ ID NOs: 13 and 14 as primers. This DNA fragment was treated with NdeI/XbaI, and the resulting DNA fragment and an NdeI/XbaI treatment product of pTrpT were ligated. *Escherichia coli* JM109 was then transformed with this ligation solution, and strains having the target plasmid were selected from ampicillin-resistant strains. The plasmid was designated as pTrpT_Sm_aet.

One loopful cells of *Escherichia coli* JM109 having pTrpT_Sm_aet was inoculated into an ordinary test tube containing 3 ml of a medium (glucose 2 g/l, yeast extract 10 g/l, casamino acid 10 g/l, ammonium sulfate 5 g/l, potassium dihydrogen phosphate 3 g/l, dipotassium hydrogen phosphate 1 g/l, magnesium sulfate heptahydrate 0.5 g/l and ampicillin 100 mg/l) and the cultivation was performed at 25° C. for 20 hours. It was verified that a cloned gene having an L-alanyl-L-glutamine production activity of 2.1 Upper ml of culture broth was expressed by *Escherichia coli*. Furthermore, no activity was detected for a transformant containing only pTrpT used as a control.

(Prediction of Signal Sequence)

When the amino acid sequence of SEQ ID NO: 12 described in the Sequence Listing was analyzed with the Signal P v 1.1 program (Protein Engineering, Vol. 12, No. 1, pp. 3-9, 1999), it was predicted that numbers 1 to 20 in amino acid sequence was operated as a signal to secrete into the periplasm, while the mature protein was estimated to be downstream of amino acid number 21.

(Confirmation of Signal Sequence)

One loopful cells of *Escherichia coli* JM109, having pTrpT_Sm_aet, was inoculated into ordinary test tubes containing 50 ml of a medium (glucose 2 g/l, yeast extract 10 g/l, casamino acid 10 g/l, ammonium sulfate 5 g/l, potassium dihydrogen phosphate 3 g/l, dipotassium hydrogen phosphate 1 g/l, magnesium sulfate heptahydrate 0.5 g/l and ampicillin 100 mg/l) and main cultivation was performed at 25° C. for 20 hours.

Hereinafter, procedures after centrifugal separation were carried out either on ice or at 4° C. After the cultivation, the microbial cells were separated from the culture broth by centrifugation, washed with 100 mM phosphate buffer (pH 7), and then suspended in the same buffer. The microbial cells were then subjected to ultrasonic disrupting treatment for 20 minutes at 195 W, the ultrasonically disrupted solution was centrifuged (12,000 rpm, 30 minutes) to remove the debris and obtain a soluble fraction. The resulting soluble fraction was applied to a CHT-II column manufactured by Biorad) pre-equilibrated with 100 mM phosphate buffer (pH 7), and enzyme was eluted at a linear concentration gradient with 500 mM phosphate buffer.

A solution obtained by mixing the active fraction with 5 fold volumes of 2 M ammonium sulfate and 100 mM phosphate buffer was applied to a Resource-PHE column (manufactured by Amersham) pre-equilibrated with 2 M ammonium sulfate and 100 mM phosphate buffer, and an enzyme was eluted at a linear concentration gradient by 2 to 0 M ammonium sulfate to obtain an active fraction solution. As a result of these procedures, it was verified that the peptide-forming enzyme was electrophoretically uniformly purified.

When the amino acid sequence of the aforementioned peptide-forming enzyme was determined by Edman's decomposition method, the amino acid sequence of SEQ ID NO: 15 was obtained, and the mature protein was verified to be downstream of amino acid number 21 as was predicted by the SignalP v 1.1 program.

INDUSTRIAL APPLICABILITY

According to the present invention, tripeptides can be produced easily using enzymes. According to the method of the present invention, peptides that are equal to or longer than tripeptides can be produced easily, inexpensively in high yields while mitigating complex synthesis methods such as introduction and elimination of protecting groups.

Sequence Listing

SEQ ID NO: 3: Synthetic primer 1
SEQ ID NO: 4: Synthetic primer 2
SEQ ID NO: 5: Gene encoding a peptide-forming enzyme
SEQ ID NO: 7: Synthetic primer for preparing pTrpT
SEQ ID NO: 8: Synthetic primer for preparing pTrpT
SEQ ID NO: 9: Synthetic primer for preparing pTrpT_Gtg2
SEQ ID NO: 10: Synthetic primer for preparing pTrpT_Gtg2
SEQ ID NO: 11: Gene encoding a peptide-forming enzyme
SEQ ID NO: 13: Synthetic primer for preparing pTrpT_S-m_aet
SEQ ID NO: 14: Synthetic primer for preparing pTrpT_S-m_aet

The invention claimed is:

1. A method for producing a peptide having three or more amino acid residues, comprising:

forming the peptide having three or more amino acid residues with an enzyme or enzyme-containing substance, wherein the enzyme or enzyme-containing substance has an ability to use as substrates an amine component having two or more amino acid residues and a carboxy component, to form a peptide having one more peptide bond than the amine component;

wherein said carboxy component is an amino acid ester or an amino acid amide;

wherein said amine component is selected from the group consisting of an unprotected peptide having two or more amino acid residues, a C-protected peptide having two or more amino acid residues, and a peptide having two or more amino acid residues and having a C-terminal amine in place of an amino acid;

wherein said carboxy component has an unprotected amino group;

wherein said peptide having three or more amino acid residues contains an amino acid residue derived from said carboxy component at the N-terminus thereof; and wherein the enzyme or enzyme in said enzyme-containing substance is selected from the group consisting of a protein having the amino acid sequence consisting of amino acid residues 23 to 616 of the amino acid sequence of SEQ ID NO: 6, a protein having an amino acid sequence including substitution, deletion, insertion, and/or addition of one to ten amino acids in the amino acid sequence consisting of amino acid residues 23 to 616 of the amino acid sequence of SEQ ID NO: 6, a protein having the amino acid sequence of SEQ ID NO: 6, a protein containing a mature protein region, the protein having an amino acid sequence including substitution, deletion, insertion, and/or addition of one to ten amino acids in the amino acid sequence of SEQ ID NO: 6, a product of a microbe that has been transformed so as to express a protein encoded by the polynucleotide consisting of nucleotides 127 to 1908 of the nucleotide sequence of SEQ ID NO: 5, and a product of a microbe that has been transformed so as to express a protein encoded by the polynucleotide consisting of nucleotides 61 to 1908 of the nucleotide sequence of SEQ ID NO: 5.

2. The method for producing a peptide according to claim 1, wherein said enzyme is a protein having the amino acid sequence consisting of amino acid residues numbers 23 to 616 of the amino acid sequence described in SEQ ID NO: 6.

3. The method for producing a peptide according to claim 1, wherein said enzyme is a protein having an amino acid sequence including substitution, deletion, insertion, and/or addition of one to ten of amino acids in the amino acid sequence consisting of amino acid residues 23 to 616 of the amino acid sequence described in SEQ ID NO: 6.

4. The method for producing a peptide according to claim 1, wherein said enzyme is a protein having the amino acid sequence of SEQ ID NO: 6.

5. The method for producing a peptide according to claim 1, wherein said enzyme is a protein containing a mature protein region, the protein having an amino acid sequence including substitution, deletion, insertion, and/or addition of one to ten amino acids in the amino acid sequence of SEQ ID NO: 6.

6. The method for producing a peptide according to claim 1, wherein the microbe is *Escherichia coli*.

7. The method for producing a peptide according to claim 1, wherein said enzyme is a product of a microbe that has been transformed so as to express a protein encoded by the polynucleotide consisting of nucleotides 127 to 1908 of the nucleotide sequence of SEQ ID NO: 5.

8. The method for producing a peptide according to claim 7, wherein the microbe is *Escherichia coli*.

9. The method for producing a peptide according to claim 1, wherein said enzyme is a product of a microbe that has been transformed so as to express a protein encoded by the polynucleotide consisting of nucleotides 61 to 1908 of the nucleotide sequence of SEQ ID NO: 5.

10. The method for producing a peptide according to claim 9, wherein the microbe is *Escherichia coli*.

11. The method for producing a peptide according to claim 1, wherein the carboxy component comprises at least one amino acid ester selected from the group consisting of an L-alanine ester, a glycine ester, an L-threonine ester, an L-tyrosine ester and a D-alanine ester.

* * * * *

```
                        SEQUENCE LISTING

<160> NUMBER OF SEQ ID NOS: 14

<210> SEQ ID NO 1
<211> LENGTH: 9
<212> TYPE: PRT
<213> ORGANISM: Empedobacter brevis

<400> SEQUENCE: 1

Leu Phe Thr Ala Ile Tyr Gln Pro Lys
1               5

<210> SEQ ID NO 2
<211> LENGTH: 9
<212> TYPE: PRT
<213> ORGANISM: Empedobacter brevis

<400> SEQUENCE: 2

Thr Asn Val Thr Tyr Thr Met Pro Asp
1               5

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = any nucleotide
<220> FEATURE:
<221> NAME/KEY: misc_feature
<222> LOCATION: (9)..(9)
<223> OTHER INFORMATION: n = any nucleotide

<400> SEQUENCE: 3
ttyacngcna thtaycarcc                                                  20

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA
```

```
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (15)..(15)
<223> OTHER INFORMATION: n = any nucleotide
<220> FEATURE:
<221> NAME/KEY: misc_feature
<222> LOCATION: (18)..(18)
<223> OTHER INFORMATION: n = any nucleotide

<400> SEQUENCE: 4
tcnggcatng trtangtnac rtt                                         23

<210> SEQ ID NO 5
<211> LENGTH: 2024
<212> TYPE: DNA
<213> ORGANISM: Empedobacter brevis
<220> FEATURE:
<221> NAME/KEY: CDS
<222> LOCATION: (61)..(1908)
<223> OTHER INFORMATION:

<400> SEQUENCE: 5
atttcttaat aaaaactgaa atcttaatac atttatacta tcgtaaaatt tattgaacac    60 gtg aaa aaa tta aca tta aaa gta act cta ctt aca ctt ttg ttg gga    108
Val Lys Lys Leu Thr Leu Lys Val Thr Leu Leu Thr Leu Leu Leu Gly
1               5                   10                  15 agt aca gtt gga ttt gcg caa gat gca aaa gca gat tct gct tat gtg    156
Ser Thr Val Gly Phe Ala Gln Asp Ala Lys Ala Asp Ser Ala Tyr Val
            20                  25                  30 cgc gac aat tac gaa aaa ata gaa caa gta att ccg atg cgc gat ggt    204
Arg Asp Asn Tyr Glu Lys Ile Glu Gln Val Ile Pro Met Arg Asp Gly
        35                  40                  45 aca aag tta ttt aca gct att tat cag cca aaa gat aaa aca aaa caa    252
Thr Lys Leu Phe Thr Ala Ile Tyr Gln Pro Lys Asp Lys Thr Lys Gln
    50                  55                  60 tat ccc gtt ttg tta aat cgt acg cct tat aca gtt gcg cct tat ggt    300
Tyr Pro Val Leu Leu Asn Arg Thr Pro Tyr Thr Val Ala Pro Tyr Gly
65                  70                  75                  80 gta aat gaa tac aag aaa tcg tta gga aat ttt cct aca gaa atg cgc    348
Val Asn Glu Tyr Lys Lys Ser Leu Gly Asn Phe Pro Thr Glu Met Arg
                85                  90                  95 gaa ggt ttt att ttt gtt tac caa gat gtg aga gga aaa tgg atg agc    396
Glu Gly Phe Ile Phe Val Tyr Gln Asp Val Arg Gly Lys Trp Met Ser
            100                 105                 110 gaa ggc gaa ttt gaa gat gtt cga cct ata aat cct tca aaa agt aaa    444
Glu Gly Glu Phe Glu Asp Val Arg Pro Ile Asn Pro Ser Lys Ser Lys
        115                 120                 125 aag gca att gac gaa agc aca gat aca ttt gat acg cta gaa tgg ctt    492
Lys Ala Ile Asp Glu Ser Thr Asp Thr Phe Asp Thr Leu Glu Trp Leu
    130                 135                 140 gct aaa aac ttg aag aat tac acg aaa aaa gct gga att tat gga att    540
Ala Lys Asn Leu Lys Asn Tyr Thr Lys Lys Ala Gly Ile Tyr Gly Ile
145                 150                 155                 160 tcg tat cct ggt ttt tat tcg aca atg agt ttg gtt aat tcg cat cca    588
Ser Tyr Pro Gly Phe Tyr Ser Thr Met Ser Leu Val Asn Ser His Pro
                165                 170                 175
```

-continued

| | | |
|---|---|---|
| act cta aaa gcc gtt tcg cca caa gcg ccc gtt acc aat tgg ttt tta<br>Thr Leu Lys Ala Val Ser Pro Gln Ala Pro Val Thr Asn Trp Phe Leu<br>        180                        185                      190 | | 636 |
| ggt gac gat ttt cat cat aat gga gtt tta ttc ttg aat gat tct ttc<br>Gly Asp Asp Phe His His Asn Gly Val Leu Phe Leu Asn Asp Ser Phe<br>            195                      200                    205 | | 684 |
| tca ttt atg act ttt ttt ggt gta aaa cgt ccg caa cca att acg cca<br>Ser Phe Met Thr Phe Phe Gly Val Lys Arg Pro Gln Pro Ile Thr Pro<br>210                      215                    220 | | 732 |
| gat aaa ggt ccg aaa cgt ttt gaa tat cca ata aaa gat aat tat aga<br>Asp Lys Gly Pro Lys Arg Phe Glu Tyr Pro Ile Lys Asp Asn Tyr Arg<br>225                      230                    235                    240 | | 780 |
| ttt tat gca agt ggc tct gta aaa gag ttg aaa gat aaa tat ttg caa<br>Phe Tyr Ala Ser Gly Ser Val Lys Glu Leu Lys Asp Lys Tyr Leu Gln<br>                      245                    250                    255 | | 828 |
| gat aat atc aag ttt tac aat gat tta ttt gcg cat cca gat tac gat<br>Asp Asn Ile Lys Phe Tyr Asn Asp Leu Phe Ala His Pro Asp Tyr Asp<br>                      260                    265                    270 | | 876 |
| caa ttt tgg caa gat cgt aat gtt tta cca cat tta act aac gtg caa<br>Gln Phe Trp Gln Asp Arg Asn Val Leu Pro His Leu Thr Asn Val Gln<br>                  275                    280                    285 | | 924 |
| cct gct gta atg acg gtt gga ggt ttt ttt gat gca gaa gat gtc tac<br>Pro Ala Val Met Thr Val Gly Gly Phe Phe Asp Ala Glu Asp Val Tyr<br>        290                      295                    300 | | 972 |
| ggc gct ttc gaa acg tat aaa gca att gag aaa caa aat ccg aaa gca<br>Gly Ala Phe Glu Thr Tyr Lys Ala Ile Glu Lys Gln Asn Pro Lys Ala<br>305                      310                    315                    320 | | 1020 |
| aca aat att atg gtt gcc gga cct tgg ttt cat ggt ggt tgg gtt cgt<br>Thr Asn Ile Met Val Ala Gly Pro Trp Phe His Gly Gly Trp Val Arg<br>                          325                    330                    335 | | 1068 |
| agc aac gga agt act ttt gga gat atg caa ttt gca tcg aat aca agt<br>Ser Asn Gly Ser Thr Phe Gly Asp Met Gln Phe Ala Ser Asn Thr Ser<br>                      340                    345                    350 | | 1116 |
| gag cat tat cag caa gaa ata gaa ttg cct ttt ttt aat tat tac tta<br>Glu His Tyr Gln Gln Glu Ile Glu Leu Pro Phe Phe Asn Tyr Tyr Leu<br>                355                    360                    365 | | 1164 |
| aaa gat aaa ggt aat ttt aaa cca acc gaa gct aca att ttt att acg<br>Lys Asp Lys Gly Asn Phe Lys Pro Thr Glu Ala Thr Ile Phe Ile Thr<br>370                      375                    380 | | 1212 |
| gga tct aac gaa tgg aaa caa ttt gat gct tgg cca cca aaa aat gta<br>Gly Ser Asn Glu Trp Lys Gln Phe Asp Ala Trp Pro Pro Lys Asn Val<br>385                      390                    395                    400 | | 1260 |
| aca aca caa aaa att tat ttg caa caa aat ggt aaa ata gct ttt aat<br>Thr Thr Gln Lys Ile Tyr Leu Gln Gln Asn Gly Lys Ile Ala Phe Asn<br>                          405                    410                    415 | | 1308 |
| aaa acc aat aca aca act act ttt gac gaa tat gtt gca gat cca aat<br>Lys Thr Asn Thr Thr Thr Thr Phe Asp Glu Tyr Val Ala Asp Pro Asn<br>                      420                    425                    430 | | 1356 |
| tct cca gtt cct tat tca gga gga gtt tta gaa act cgt tca aga gaa<br>Ser Pro Val Pro Tyr Ser Gly Gly Val Leu Glu Thr Arg Ser Arg Glu<br>                          435                    440                    445 | | 1404 |
| tat atg gtc gat gat caa cgc ttt gct tct act cgt cct gat gtt atg<br>Tyr Met Val Asp Asp Gln Arg Phe Ala Ser Thr Arg Pro Asp Val Met<br>        450                      455                    460 | | 1452 |
| gtg tat caa tct gat att ttg aca gaa gat att acg ctt gct ggt cct<br>Val Tyr Gln Ser Asp Ile Leu Thr Glu Asp Ile Thr Leu Ala Gly Pro<br>465                      470                    475                    480 | | 1500 |
| gtt atc aat cat tta gtg gtt tct act acg gga aca gac gct gat tat<br>Val Ile Asn His Leu Val Val Ser Thr Thr Gly Thr Asp Ala Asp Tyr<br>                      485                    490                    495 | | 1548 |

| | | | | | | | | | | | | | | | |
|---|---|---|---|---|---|---|---|---|---|---|---|---|---|---|---|
| gtt | gta | aaa | ttg | att | gat | gtt | tat | cct | gaa | aac | acg | cca | aaa | ttt | aat | 1596 |
| Val | Val | Lys | Leu | Ile | Asp | Val | Tyr | Pro | Glu | Asn | Thr | Pro | Lys | Phe | Asn | |
| | | | 500 | | | | | 505 | | | | | 510 | | | |
| aac | aaa | tta | atg | gct | gga | tat | caa | aat | ttg | att | cgt | gca | gaa | att | atg | 1644 |
| Asn | Lys | Leu | Met | Ala | Gly | Tyr | Gln | Asn | Leu | Ile | Arg | Ala | Glu | Ile | Met | |
| | | | 515 | | | | | 520 | | | | | 525 | | | |
| cgc | gga | aaa | tat | aga | aat | agt | ttc | tct | aac | ccc | gaa | gct | atg | gtt | ccg | 1692 |
| Arg | Gly | Lys | Tyr | Arg | Asn | Ser | Phe | Ser | Asn | Pro | Glu | Ala | Met | Val | Pro | |
| | | 530 | | | | | 535 | | | | | 540 | | | | |
| aat | aaa | gaa | aca | aat | gta | acg | tac | acg | atg | cca | gat | gtt | gga | cat | aca | 1740 |
| Asn | Lys | Glu | Thr | Asn | Val | Thr | Tyr | Thr | Met | Pro | Asp | Val | Gly | His | Thr | |
| 545 | | | | | 550 | | | | | 555 | | | | | 560 | |
| ttt | aag | aaa | gga | cat | cgc | att | atg | att | caa | gtt | cag | aac | agt | tgg | ttt | 1788 |
| Phe | Lys | Lys | Gly | His | Arg | Ile | Met | Ile | Gln | Val | Gln | Asn | Ser | Trp | Phe | |
| | | | | 565 | | | | | 570 | | | | | 575 | | |
| cct | tta | gca | gat | cgc | aat | ccg | caa | caa | ttt | atg | aat | gtt | tac | gaa | gca | 1836 |
| Pro | Leu | Ala | Asp | Arg | Asn | Pro | Gln | Gln | Phe | Met | Asn | Val | Tyr | Glu | Ala | |
| | | | 580 | | | | | 585 | | | | | 590 | | | |
| act | tct | aaa | gat | tat | tta | aaa | caa | acg | caa | cga | att | tat | cat | act | tct | 1884 |
| Thr | Ser | Lys | Asp | Tyr | Leu | Lys | Gln | Thr | Gln | Arg | Ile | Tyr | His | Thr | Ser | |
| | | | 595 | | | | | 600 | | | | | 605 | | | |

| | | | | | | |
|---|---|---|---|---|---|---|
| tat | atc | gaa | att | ccg | gta | ttg aaa taacaaaaaa atccagctaa ttagctggat | 1938 |
| Tyr | Ile | Glu | Ile | Pro | Val | Leu Lys | |
| | 610 | | | | | 615 | | tttttttata atgttacttt tcctatttt cctttattc caactaaaat tacatatttt  1998 ttatcgggcg aaaccgtaca agtatg  2024

<210> SEQ ID NO 6
<211> LENGTH: 616
<212> TYPE: PRT
<213> ORGANISM: Empedobacter brevis

<400> SEQUENCE: 6

Val Lys Lys Leu Thr Leu Lys Val Thr Leu Leu Thr Leu Leu Leu Gly
1               5                   10                  15

Ser Thr Val Gly Phe Ala Gln Asp Ala Lys Ala Asp Ser Ala Tyr Val
            20                  25                  30

Arg Asp Asn Tyr Glu Lys Ile Glu Gln Val Ile Pro Met Arg Asp Gly
        35                  40                  45

Thr Lys Leu Phe Thr Ala Ile Tyr Gln Pro Lys Asp Lys Thr Lys Gln
    50                  55                  60

Tyr Pro Val Leu Leu Asn Arg Thr Pro Tyr Thr Val Ala Pro Tyr Gly
65                  70                  75                  80

Val Asn Glu Tyr Lys Lys Ser Leu Gly Asn Phe Pro Thr Glu Met Arg
                85                  90                  95

Glu Gly Phe Ile Phe Val Tyr Gln Asp Val Arg Gly Lys Trp Met Ser
            100                 105                 110

Glu Gly Glu Phe Glu Asp Val Arg Pro Ile Asn Pro Ser Lys Ser Lys
        115                 120                 125

Lys Ala Ile Asp Glu Ser Thr Asp Thr Phe Asp Thr Leu Glu Trp Leu
    130                 135                 140

Ala Lys Asn Leu Lys Asn Tyr Thr Lys Lys Ala Gly Ile Tyr Gly Ile
145                 150                 155                 160

Ser Tyr Pro Gly Phe Tyr Ser Thr Met Ser Leu Val Asn Ser His Pro
                165                 170                 175

Thr Leu Lys Ala Val Ser Pro Gln Ala Pro Val Thr Asn Trp Phe Leu

-continued

```
                180                 185                 190
Gly Asp Asp Phe His His Asn Gly Val Leu Phe Leu Asn Asp Ser Phe
            195                 200                 205
Ser Phe Met Thr Phe Phe Gly Val Lys Arg Pro Gln Pro Ile Thr Pro
210                 215                 220
Asp Lys Gly Pro Lys Arg Phe Glu Tyr Pro Ile Lys Asp Asn Tyr Arg
225                 230                 235                 240
Phe Tyr Ala Ser Gly Ser Val Lys Glu Leu Lys Asp Lys Tyr Leu Gln
            245                 250                 255
Asp Asn Ile Lys Phe Tyr Asn Asp Leu Phe Ala His Pro Asp Tyr Asp
            260                 265                 270
Gln Phe Trp Gln Asp Arg Asn Val Leu Pro His Leu Thr Asn Val Gln
            275                 280                 285
Pro Ala Val Met Thr Val Gly Gly Phe Phe Asp Ala Glu Asp Val Tyr
            290                 295                 300
Gly Ala Phe Glu Thr Tyr Lys Ala Ile Glu Lys Gln Asn Pro Lys Ala
305                 310                 315                 320
Thr Asn Ile Met Val Ala Gly Pro Trp Phe His Gly Gly Trp Val Arg
            325                 330                 335
Ser Asn Gly Ser Thr Phe Gly Asp Met Gln Phe Ala Ser Asn Thr Ser
            340                 345                 350
Glu His Tyr Gln Gln Glu Ile Glu Leu Pro Phe Phe Asn Tyr Tyr Leu
            355                 360                 365
Lys Asp Lys Gly Asn Phe Lys Pro Thr Glu Ala Thr Ile Phe Ile Thr
370                 375                 380
Gly Ser Asn Glu Trp Lys Gln Phe Asp Ala Trp Pro Pro Lys Asn Val
385                 390                 395                 400
Thr Thr Gln Lys Ile Tyr Leu Gln Gln Asn Gly Lys Ile Ala Phe Asn
            405                 410                 415
Lys Thr Asn Thr Thr Thr Phe Asp Glu Tyr Val Ala Asp Pro Asn
            420                 425                 430
Ser Pro Val Pro Tyr Ser Gly Gly Val Leu Glu Thr Arg Ser Arg Glu
            435                 440                 445
Tyr Met Val Asp Asp Gln Arg Phe Ala Ser Thr Arg Pro Asp Val Met
450                 455                 460
Val Tyr Gln Ser Asp Ile Leu Thr Glu Asp Ile Thr Leu Ala Gly Pro
465                 470                 475                 480
Val Ile Asn His Leu Val Val Ser Thr Thr Gly Thr Asp Ala Asp Tyr
            485                 490                 495
Val Val Lys Leu Ile Asp Val Tyr Pro Glu Asn Thr Pro Lys Phe Asn
            500                 505                 510
Asn Lys Leu Met Ala Gly Tyr Gln Asn Leu Ile Arg Ala Glu Ile Met
            515                 520                 525
Arg Gly Lys Tyr Arg Asn Ser Phe Ser Asn Pro Glu Ala Met Val Pro
            530                 535                 540
Asn Lys Glu Thr Asn Val Thr Tyr Thr Met Pro Asp Val Gly His Thr
545                 550                 555                 560
Phe Lys Lys Gly His Arg Ile Met Ile Gln Val Gln Asn Ser Trp Phe
            565                 570                 575
Pro Leu Ala Asp Arg Asn Pro Gln Gln Phe Met Asn Val Tyr Glu Ala
            580                 585                 590
Thr Ser Lys Asp Tyr Leu Lys Gln Thr Gln Arg Ile Tyr His Thr Ser
            595                 600                 605
```

-continued

```
Tyr Ile Glu Ile Pro Val Leu Lys
    610             615

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gtatcacgag gccctagctg tggtgtcatg gtcggtgatc                          40

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
ttcggggatt ccatatgata cccttttttac gtgaacttgc                         40

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
gggaattcca tatgaaaaaa ttaacattaa aagtaact                            38

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
gggggctgca gtacttgtac ggtttcgccc gataaa                              36

<210> SEQ ID NO 11
<211> LENGTH: 1935
<212> TYPE: DNA
<213> ORGANISM: Sphingobacterium sp.
<220> FEATURE:
<221> NAME/KEY: CDS
<222> LOCATION: (61)..(1917)
<223> OTHER INFORMATION:

<400> SEQUENCE: 11
gaaaccaagt gtaaaattat aatttacacc aaagaatgta ctgaacaaat aattatctga    60 atg aaa aat aca att tcg tgc cta act tta gcg ctt tta agc gca agc    108
Met Lys Asn Thr Ile Ser Cys Leu Thr Leu Ala Leu Leu Ser Ala Ser
1               5                   10                  15 cag tta cat gct caa aca gct gcc gac tcg gct tat gtt aga gat cat    156
Gln Leu His Ala Gln Thr Ala Ala Asp Ser Ala Tyr Val Arg Asp His
            20                  25                  30 tat gaa aag acc gaa gta gca att ccc atg cga gat ggg aaa aaa tta    204
Tyr Glu Lys Thr Glu Val Ala Ile Pro Met Arg Asp Gly Lys Lys Leu
        35                  40                  45 ttt act gcg atc tac agt cca aaa gac aaa tcc aag aaa tat cca gtt    252
```

-continued

```
Phe Thr Ala Ile Tyr Ser Pro Lys Asp Lys Ser Lys Lys Tyr Pro Val
     50                  55                  60 ttg ctc aat aga acg ccc tac acg gtt tca cct tat ggg cag aac gaa      300
Leu Leu Asn Arg Thr Pro Tyr Thr Val Ser Pro Tyr Gly Gln Asn Glu
 65                  70                  75                  80 tat aaa aaa agc ttg gga aac ttt ccc caa atg atg cgt gaa ggc tat      348
Tyr Lys Lys Ser Leu Gly Asn Phe Pro Gln Met Met Arg Glu Gly Tyr
                 85                  90                  95 att ttc gtt tac cag gat gtc cgt ggc aag tgg atg agc gaa ggt gat      396
Ile Phe Val Tyr Gln Asp Val Arg Gly Lys Trp Met Ser Glu Gly Asp
            100                 105                 110 ttt gaa gat ata cgt ccg acc acg tac agc aaa gat aaa aaa gca atc      444
Phe Glu Asp Ile Arg Pro Thr Thr Tyr Ser Lys Asp Lys Lys Ala Ile
        115                 120                 125 gat gaa agt acg gat acc tat gat gcg ctt gaa tgg tta cag aaa aat      492
Asp Glu Ser Thr Asp Thr Tyr Asp Ala Leu Glu Trp Leu Gln Lys Asn
130                 135                 140 ctc aaa aac tat aat ggc aaa gcc ggg ctc tat ggg att tcc tat cca      540
Leu Lys Asn Tyr Asn Gly Lys Ala Gly Leu Tyr Gly Ile Ser Tyr Pro
145                 150                 155                 160 ggc ttc tat tct acc gtc gga ttg gtc aaa aca cac ccg agc ttg aag      588
Gly Phe Tyr Ser Thr Val Gly Leu Val Lys Thr His Pro Ser Leu Lys
                165                 170                 175 gca gtc tcc cca cag gct ccc gta aca gac tgg tat atc ggc gac gac      636
Ala Val Ser Pro Gln Ala Pro Val Thr Asp Trp Tyr Ile Gly Asp Asp
            180                 185                 190 ttc cac cat aat ggc gta ttg ttt ctt cag gat gca ttt aca ttc atg      684
Phe His His Asn Gly Val Leu Phe Leu Gln Asp Ala Phe Thr Phe Met
        195                 200                 205 tca acc ttt ggt gtc cct cgt cca aaa ccc att aca ccg gat caa ttt      732
Ser Thr Phe Gly Val Pro Arg Pro Lys Pro Ile Thr Pro Asp Gln Phe
210                 215                 220 aag ggc aaa att cag atc aaa gaa gcc gat aaa tat aac ttt ttt gca      780
Lys Gly Lys Ile Gln Ile Lys Glu Ala Asp Lys Tyr Asn Phe Phe Ala
225                 230                 235                 240 gaa gca gga aca gcg cgg gaa ctc aaa gaa aag tat ttt ggt gac tcc      828
Glu Ala Gly Thr Ala Arg Glu Leu Lys Glu Lys Tyr Phe Gly Asp Ser
                245                 250                 255 gta caa ttt tgg aat gac ctg ttt aag cat ccc gac tat gat gat ttt      876
Val Gln Phe Trp Asn Asp Leu Phe Lys His Pro Asp Tyr Asp Asp Phe
            260                 265                 270 tgg aaa tcg cgt gtg atc acg aat tct tta cag gag gta aaa cca gct      924
Trp Lys Ser Arg Val Ile Thr Asn Ser Leu Gln Glu Val Lys Pro Ala
        275                 280                 285 gtg atg gtg gtt ggt ggt ttc ttt gac gcg gaa gat gct tat gga aca      972
Val Met Val Val Gly Gly Phe Phe Asp Ala Glu Asp Ala Tyr Gly Thr
290                 295                 300 ttt aag acc tac caa tcg att gag gat aaa agc aaa aaa aac aac tcg     1020
Phe Lys Thr Tyr Gln Ser Ile Glu Asp Lys Ser Lys Lys Asn Asn Ser
305                 310                 315                 320 att tta gtc gcg gga cct tgg tat cat ggc ggt tgg gtt cgt gca gaa     1068
Ile Leu Val Ala Gly Pro Trp Tyr His Gly Gly Trp Val Arg Ala Glu
                325                 330                 335 gga aac tat tta ggt gat atc caa ttt gag aaa aaa acc agt att act     1116
Gly Asn Tyr Leu Gly Asp Ile Gln Phe Glu Lys Lys Thr Ser Ile Thr
            340                 345                 350 tat cag gaa caa ttt gaa caa cca ttt ttc aaa tat tac cta aaa gat     1164
Tyr Gln Glu Gln Phe Glu Gln Pro Phe Phe Lys Tyr Tyr Leu Lys Asp
        355                 360                 365
```

```
gaa gga aac ttc gcc cct tcc gaa gct aac att ttt gtt tca ggc agc     1212
Glu Gly Asn Phe Ala Pro Ser Glu Ala Asn Ile Phe Val Ser Gly Ser
    370                 375                 380 aac gaa tgg aaa cat ttc gaa cag tgg cca cca aaa aat gta gag aca     1260
Asn Glu Trp Lys His Phe Glu Gln Trp Pro Pro Lys Asn Val Glu Thr
385                 390                 395                 400 aaa aaa cta tac ttc caa cct cag ggg aaa ctt gga ttt gac aaa gtt     1308
Lys Lys Leu Tyr Phe Gln Pro Gln Gly Lys Leu Gly Phe Asp Lys Val
                405                 410                 415 caa cgt aca gat tcc tgg gat gaa tat gta aca gac cct aat aaa cct     1356
Gln Arg Thr Asp Ser Trp Asp Glu Tyr Val Thr Asp Pro Asn Lys Pro
            420                 425                 430 gtt ccg cat caa ggt ggg gta att caa aac cga aca cgg gag tat atg     1404
Val Pro His Gln Gly Gly Val Ile Gln Asn Arg Thr Arg Glu Tyr Met
        435                 440                 445 gta gat gat caa cgt ttc gcg gct agt cgc cct gat gtc atg gtt tat     1452
Val Asp Asp Gln Arg Phe Ala Ala Ser Arg Pro Asp Val Met Val Tyr
450                 455                 460 caa acg gaa ccg ttg acg gag gac ctg acg ata gta ggc cca atc aaa     1500
Gln Thr Glu Pro Leu Thr Glu Asp Leu Thr Ile Val Gly Pro Ile Lys
465                 470                 475                 480 aac ttt ctc aaa gtt tct tca aca gga aca gac gcg gac tat gtt gtc     1548
Asn Phe Leu Lys Val Ser Ser Thr Gly Thr Asp Ala Asp Tyr Val Val
                485                 490                 495 aaa ctg att gac gtt tat ccg aat gat gca gca agt tat caa gga aaa     1596
Lys Leu Ile Asp Val Tyr Pro Asn Asp Ala Ala Ser Tyr Gln Gly Lys
            500                 505                 510 aca atg gct gga tat caa atg atg gta cgt ggt gag atc atg gcg ggg     1644
Thr Met Ala Gly Tyr Gln Met Met Val Arg Gly Glu Ile Met Ala Gly
        515                 520                 525 aaa tac cga aat ggt ttc gat aaa gcg cag gcc ttg act cca ggt atg     1692
Lys Tyr Arg Asn Gly Phe Asp Lys Ala Gln Ala Leu Thr Pro Gly Met
530                 535                 540 gtc gaa aag gtg aat ttt gaa atg cca gac gtt gcg cat acc ttc aaa     1740
Val Glu Lys Val Asn Phe Glu Met Pro Asp Val Ala His Thr Phe Lys
545                 550                 555                 560 aaa gga cat cgc att atg gtt cag gta caa aac tca tgg ttt ccg ctg     1788
Lys Gly His Arg Ile Met Val Gln Val Gln Asn Ser Trp Phe Pro Leu
                565                 570                 575 gca gaa cga aat cca cag gtg ttt tta gca cct tat aca gct acc aaa     1836
Ala Glu Arg Asn Pro Gln Val Phe Leu Ala Pro Tyr Thr Ala Thr Lys
            580                 585                 590 gct gat ttc cgc aaa gct acc caa cgt att ttt cac gat gtg aac aat     1884
Ala Asp Phe Arg Lys Ala Thr Gln Arg Ile Phe His Asp Val Asn Asn
        595                 600                 605 gcc aca tac atc gaa ttt tct gtc ctc aaa gat tagcaggtaa attcgaaa    1935
Ala Thr Tyr Ile Glu Phe Ser Val Leu Lys Asp
610                 615

<210> SEQ ID NO 12
<211> LENGTH: 619
<212> TYPE: PRT
<213> ORGANISM: Sphingobacterium sp.

<400> SEQUENCE: 12

Met Lys Asn Thr Ile Ser Cys Leu Thr Leu Ala Leu Leu Ser Ala Ser
1               5                   10                  15

Gln Leu His Ala Gln Thr Ala Ala Asp Ser Ala Tyr Val Arg Asp His
                20                  25                  30

Tyr Glu Lys Thr Glu Val Ala Ile Pro Met Arg Asp Gly Lys Lys Leu
```

```
                35                  40                  45
Phe Thr Ala Ile Tyr Ser Pro Lys Asp Lys Ser Lys Lys Tyr Pro Val
 50                  55                  60

Leu Leu Asn Arg Thr Pro Tyr Thr Val Ser Pro Tyr Gly Gln Asn Glu
 65                  70                  75                  80

Tyr Lys Lys Ser Leu Gly Asn Phe Pro Gln Met Met Arg Glu Gly Tyr
                 85                  90                  95

Ile Phe Val Tyr Gln Asp Val Arg Gly Lys Trp Met Ser Glu Gly Asp
                100                 105                 110

Phe Glu Asp Ile Arg Pro Thr Thr Tyr Ser Lys Asp Lys Lys Ala Ile
                115                 120                 125

Asp Glu Ser Thr Asp Thr Tyr Asp Ala Leu Glu Trp Leu Gln Lys Asn
130                 135                 140

Leu Lys Asn Tyr Asn Gly Lys Ala Gly Leu Tyr Gly Ile Ser Tyr Pro
145                 150                 155                 160

Gly Phe Tyr Ser Thr Val Gly Leu Val Lys Thr His Pro Ser Leu Lys
                165                 170                 175

Ala Val Ser Pro Gln Ala Pro Val Thr Asp Trp Tyr Ile Gly Asp Asp
                180                 185                 190

Phe His His Asn Gly Val Leu Phe Leu Gln Asp Ala Phe Thr Phe Met
                195                 200                 205

Ser Thr Phe Gly Val Pro Arg Pro Lys Pro Ile Thr Pro Asp Gln Phe
210                 215                 220

Lys Gly Lys Ile Gln Ile Lys Glu Ala Asp Lys Tyr Asn Phe Phe Ala
225                 230                 235                 240

Glu Ala Gly Thr Ala Arg Glu Leu Lys Glu Lys Tyr Phe Gly Asp Ser
                245                 250                 255

Val Gln Phe Trp Asn Asp Leu Phe Lys His Pro Asp Tyr Asp Asp Phe
                260                 265                 270

Trp Lys Ser Arg Val Ile Thr Asn Ser Leu Gln Glu Val Lys Pro Ala
                275                 280                 285

Val Met Val Val Gly Phe Phe Asp Ala Glu Asp Ala Tyr Gly Thr
290                 295                 300

Phe Lys Thr Tyr Gln Ser Ile Glu Asp Lys Ser Lys Lys Asn Asn Ser
305                 310                 315                 320

Ile Leu Val Ala Gly Pro Trp Tyr His Gly Gly Trp Val Arg Ala Glu
                325                 330                 335

Gly Asn Tyr Leu Gly Asp Ile Gln Phe Glu Lys Lys Thr Ser Ile Thr
                340                 345                 350

Tyr Gln Glu Gln Phe Glu Gln Pro Phe Phe Lys Tyr Tyr Leu Lys Asp
                355                 360                 365

Glu Gly Asn Phe Ala Pro Ser Glu Ala Asn Ile Phe Val Ser Gly Ser
370                 375                 380

Asn Glu Trp Lys His Phe Glu Gln Trp Pro Pro Lys Asn Val Glu Thr
385                 390                 395                 400

Lys Lys Leu Tyr Phe Gln Pro Gln Gly Lys Leu Gly Phe Asp Lys Val
                405                 410                 415

Gln Arg Thr Asp Ser Trp Asp Glu Tyr Val Thr Asp Pro Asn Lys Pro
                420                 425                 430

Val Pro His Gln Gly Gly Val Ile Gln Asn Arg Thr Arg Glu Tyr Met
                435                 440                 445

Val Asp Asp Gln Arg Phe Ala Ala Ser Arg Pro Asp Val Met Val Tyr
450                 455                 460
```

```
Gln Thr Glu Pro Leu Thr Glu Asp Leu Thr Ile Val Gly Pro Ile Lys
465                 470                 475                 480

Asn Phe Leu Lys Val Ser Ser Thr Gly Thr Asp Ala Asp Tyr Val Val
                485                 490                 495

Lys Leu Ile Asp Val Tyr Pro Asn Asp Ala Ala Ser Tyr Gln Gly Lys
                500                 505                 510

Thr Met Ala Gly Tyr Gln Met Met Val Arg Gly Glu Ile Met Ala Gly
                515                 520                 525

Lys Tyr Arg Asn Gly Phe Asp Lys Ala Gln Ala Leu Thr Pro Gly Met
                530                 535                 540

Val Glu Lys Val Asn Phe Glu Met Pro Asp Val Ala His Thr Phe Lys
545                 550                 555                 560

Lys Gly His Arg Ile Met Val Gln Val Gln Asn Ser Trp Phe Pro Leu
                565                 570                 575

Ala Glu Arg Asn Pro Gln Val Phe Leu Ala Pro Tyr Thr Ala Thr Lys
                580                 585                 590

Ala Asp Phe Arg Lys Ala Thr Gln Arg Ile Phe His Asp Val Asn Asn
                595                 600                 605

Ala Thr Tyr Ile Glu Phe Ser Val Leu Lys Asp
    610                 615

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
gggaattcca tatgaaaaat acaatttcgt                                    30

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
gctctagact aatctttgag gacagaaaa                                     29
```